US008003312B2

(12) United States Patent
Krutzik et al.

(10) Patent No.: US 8,003,312 B2

(45) Date of Patent: Aug. 23, 2011

(54) MULTIPLEX CELLULAR ASSAYS USING DETECTABLE CELL BARCODES

(75) Inventors: Peter O. Krutzik, Los Altos, CA (US); Garry Nolan, San Francisco, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 12/031,499

(22) Filed: Feb. 14, 2008

(65) Prior Publication Data

US 2008/0241820 A1 Oct. 2, 2008

Related U.S. Application Data

(60) Provisional application No. 60/901,803, filed on Feb. 16, 2007.

(51) Int. Cl.
*C12Q 1/00* (2006.01)

(52) U.S. Cl. .......................................... 435/4; 435/7.2

(58) Field of Classification Search ........................ None
See application file for complete search history.

(56) References Cited

U.S. PATENT DOCUMENTS

| | | | | |
|---|---|---|---|---|
| 2002/0182609 | A1 | 12/2002 | Arcot | |
| 2005/0069962 | A1 | 3/2005 | Archer et al. | |
| 2005/0118574 | A1 | 6/2005 | Chandler et al. | |
| 2005/0244819 | A1 * | 11/2005 | Cheng et al. | 435/5 |
| 2005/0277197 | A1 | 12/2005 | Chandler et al. | |
| 2006/0240411 | A1 | 10/2006 | Mehrpouyan et al. | |

OTHER PUBLICATIONS

Krutzik et al. Cytometry A, 2003, 55:61-70.*
Ornatsky et al. Journal of Immunological Methods, 2006, 308:68-76.*

* cited by examiner

*Primary Examiner* — Stacy B Chen

(74) *Attorney, Agent, or Firm* — Bozicevic, Field & Francis LLP; David C. Scherer

(57) ABSTRACT

We describe herein a cell-based multiplexing technique called detectable cell barcoding (DCB). In DCB, each individual sample is labeled with a different DCB signature that distinguishes each sample by one or both of detected intensity or type of detection characteristic. The samples are then combined and analyzed for a detectable characteristic of interest (e.g., presence of an analyte). By employing multiple distinct DCB labels at varying concentrations, one can perform multiplex analyses on up to hundreds or thousands (or more) of cell samples in a single reaction tube. DCB reduces reagent consumption by factors of 100-fold or more, significantly reduces data acquisition times and allows for stringent control sample analysis.

28 Claims, 9 Drawing Sheets

A.

B.

| Cell Sample | FCB1 Intensity | FCB2 Intensity |
|---|---|---|
| A1 | - | - |
| A2 | - | + |
| A3 | - | ++ |
| A4 | - | +++ |
| B1 | + | - |
| B2 | + | + |
| B3 | + | ++ |
| B4 | + | +++ |
| C1 | ++ | - |
| C2 | ++ | + |
| C3 | ++ | ++ |
| C4 | ++ | +++ |
| D1 | +++ | - |
| D2 | +++ | + |
| D3 | +++ | ++ |
| D4 | +++ | +++ |

MULTIPLEX CELLULAR ASSAYS USING DETECTABLE CELL BARCODES

FEDERALLY-SPONSORED RESEARCH OR DEVELOPMENT

This invention was made with Government support under contract HV028183 awarded by the National Institutes of Health. The Government has certain rights in this invention.

BACKGROUND OF THE INVENTION

As the scale of cellular analysis experiments expands from a few dozen samples to hundreds or even thousands of individual samples (e.g., in a high-throughput screen), several limitations are encountered, including reagent expense, analysis time, control of assay parameters between different samples, and sample acquisition throughput. Throughput has been increased by rapid auto-samplers, but such systems are not widely available (see, e.g., Kuckuck et al. Cytometry 44, 83-90 (2001); and Edwards et al. Curr. Opin. Chem. Biol. 8, 392-398 (2004), which discuss auto samplers for flow cytometers).

The present invention provides methods and compositions for improving multiple sample (e.g., high throughput) flow cytometric assays.

SUMMARY OF THE INVENTION

The present invention is drawn to multiplex cellular assays that employ Detectable Cell Barcodes (DCB). In certain embodiments, different cell samples are labeled with different amounts of a DCB marker, e.g., by treatment with different concentrations of a DCB label that binds to a cell (e.g., a cell-reactive form of a fluorophore or a cell-reactive molecular mass marker). This gives each sample a unique signature upon analysis (e.g., flow cytometric detection and/or mass spectrometer analysis). In certain embodiments, cell samples are coded with more than one DCB marker (e.g., DCB markers having distinct detection characteristics). In these embodiments, the number of different DCB signatures available increases geometrically because of multiplexing of DCB intensity with DCB detection characteristic (for example, using different channels on the flow cytometer). DCB allows the multiplex analysis of hundreds to thousands of samples (or more) in a single reaction tube, which significantly reduces regent consumption, improves the throughput of experiments, and eliminates potential sample to sample variability.

In certain embodiments, the DCB labels employed are Fluorescent Cell Barcode labels, or FCBs. While certain embodiments below are described for FCBs, other DCBs may be employed in a similar manner. For example, in certain embodiments, the DCB labels are molecular mass markers that are detected using mass spectrometry techniques. Exemplary methods for mass spectrometer analysis of cells can be found in the following: Ornatsky et al. "Multiple cellular antigen detection by ICP-MS" *J Immunol Methods.* (2006) vol. 308 pp. 68-76; Tanner et al. "Multiplex bio-assay with inductively coupled plasma mass spectrometry: Towards a massively multivariate single-cell technology", *Spectrochimica Acta Part B: Atomic Spectroscopy* (2007) vol. 62 pp. 188-195; each of which is incorporated by reference in its entirety for its description of mass spectrometer-based cell analysis.

Cells are placed into distinct wells of a 4×4 cell culture plate and contacted to distinct concentrations of FCB1 and FCB2 labels (concentrations are indicated by the depth of the triangles). (B) FCB detection. Detection of the fluorescence intensity of FCB1 and FCB2 on the cells provides a unique identifier which indicates from which cell sample a cell is derived.

Figure 2:
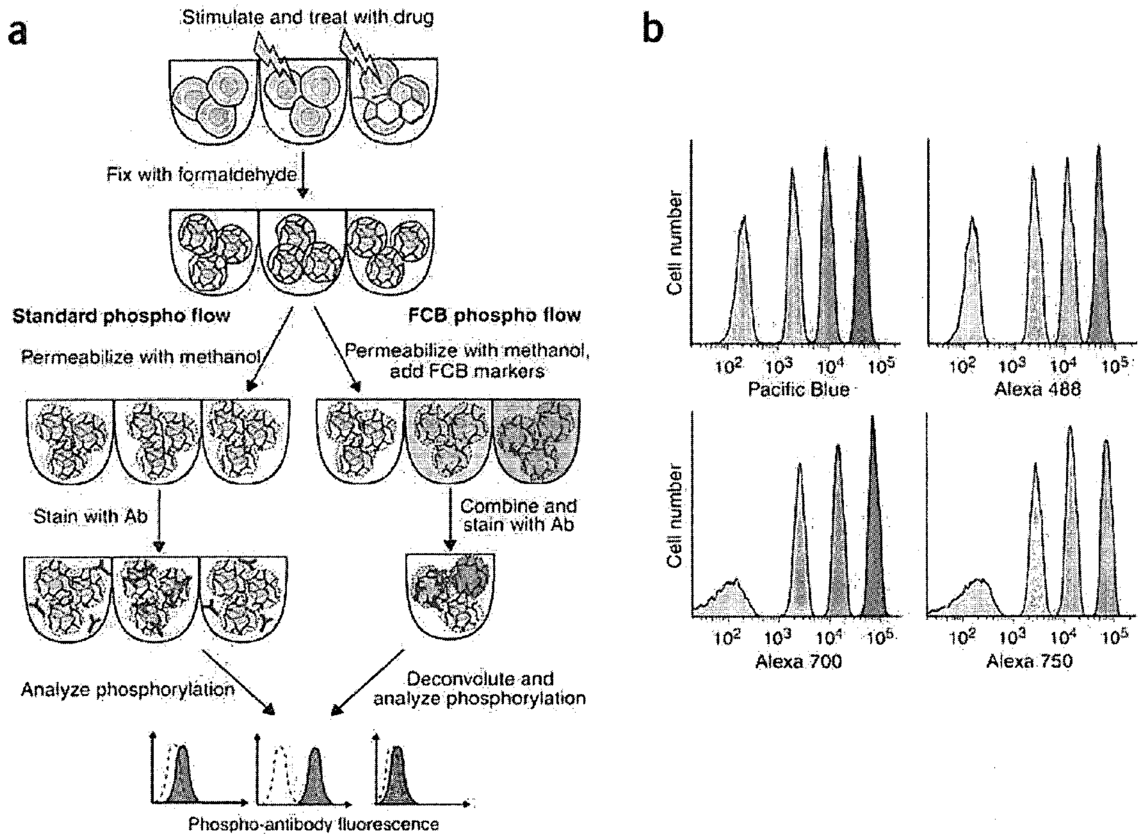

FIG. 2. Exemplary FCB technique. (a) Sample one was unstimulated, sample two was stimulated, and sample three was treated with a small-molecule inhibitor before stimulation. After fixation, cells in standard phospho flow (left) were permeabilized with cold methanol, washed and stained with phospho-specific antibodies. In the FCB technique (right side), each sample was permeabilized with 20-25° C. methanol containing a different concentration of amine-reactive fluorescent dyes (FCB markers), yielding a unique fluorescence signature for each sample. Samples were then washed, combined into one tube, and stained with antibodies. During software analysis of the acquired data, the samples were deconvoluted back to the original samples based on their FCB signature. In both standard and FCB phospho flow techniques, fluorescence of the phospho-specific antibody in each sample was measured. In the plots, dotted lines indicate autofluorescence and red histograms represent sample fluorescence. (b) Efficient labeling of four samples per marker with the FCB technique. U937 cells were fixed, then permeabilized in methanol containing 0, 0.04, 0.2 or 1 μg/ml Pacific Blue-NHS, Alexa 488-NHS, Alexa 700-NHS, or 0, 0.4, 2 or 10 μg/ml Alexa 750-NHS for 15 min at 20-25° C. After washing twice, samples stained with each FCB marker were combined and analyzed. Shown are histograms identifying the four original samples barcoded with each FCB marker. Gray peaks represent unlabeled samples (zero FCB marker). Colored peaks represent samples receiving low, medium and high amounts of the FCB marker, with color intensity correlating to FCB marker staining level.

Figure 3:
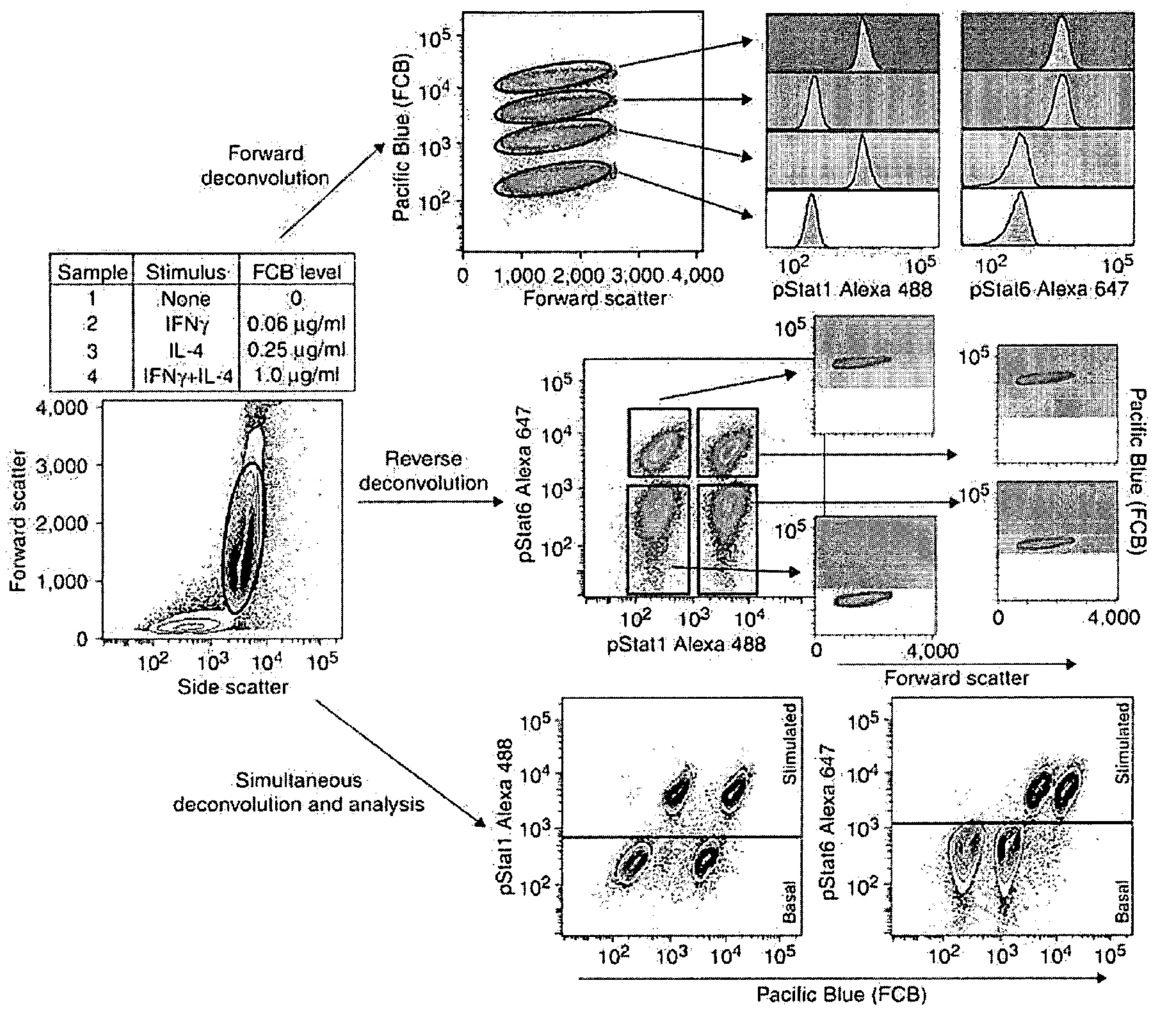

FIG. 3. Deconvolution methods for fluorescently barcoded samples. U937 cells were treated as indicated, labeled with Pacific Blue-NHS via the FCB technique, combined into one sample, and stained with pStat1 Alexa 488 and pStat6 Alexa 647 antibodies. After acquisition of samples on the flow cytometer, FCB-labeled samples can be analyzed using three methods. In forward deconvolution, the FCB marker channel is analyzed first, and the original samples are identified based on their FCB fluorescence signature (top right). The gated populations are then analyzed as individual samples for Stat1 and Stat6 phosphorylation. In reverse deconvolution, phospho-antibody staining levels are analyzed first, and populations of cells displaying the desired signaling profile are gated (middle right). The gated populations are then analyzed for their FCB fluorescence, to identify the sample origin of the cells. Simultaneous deconvolution and analysis allows rapid identification of samples that display the desired phenotype (bottom right).

Figure 4:
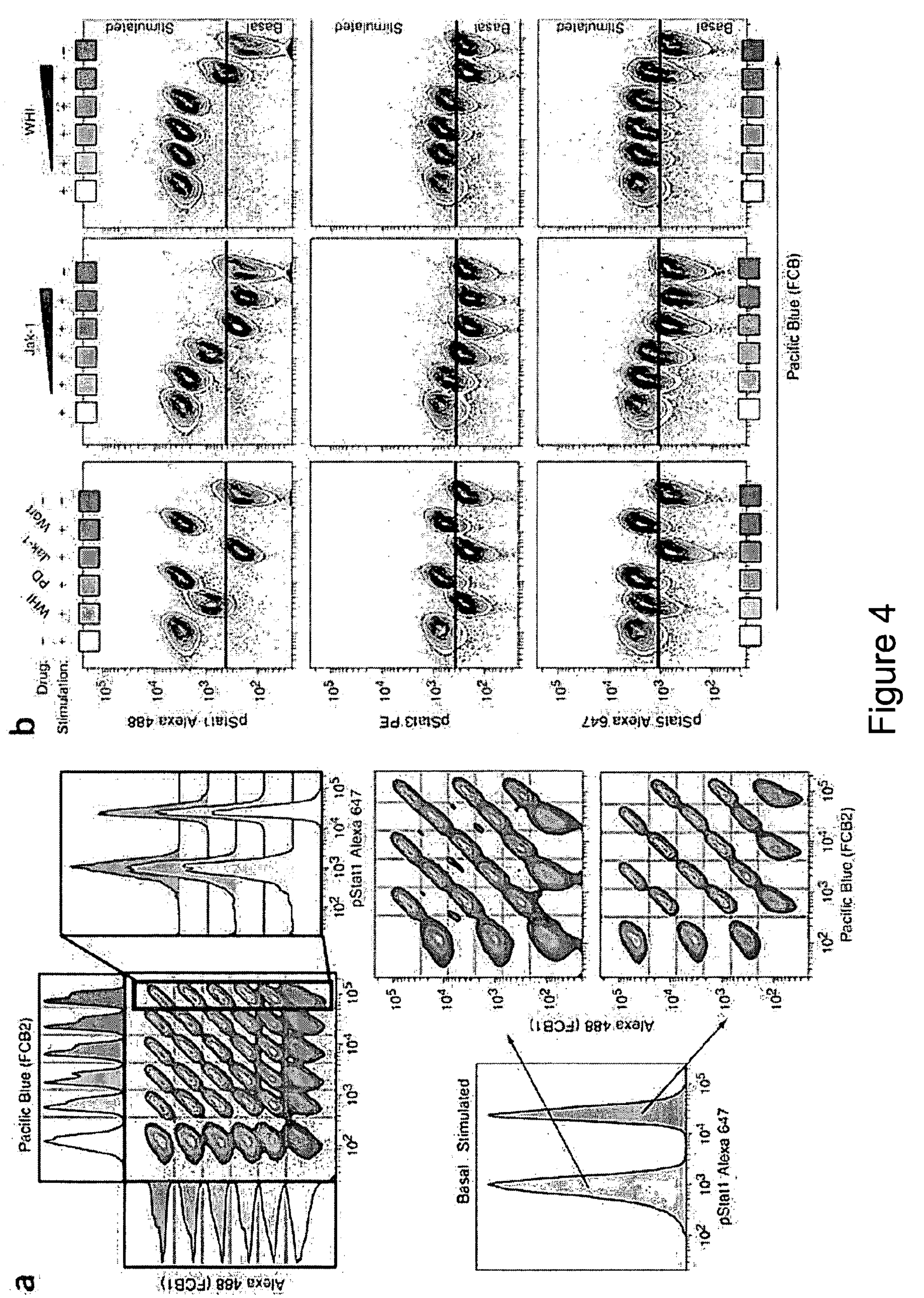

FIG. 4. FCB of 36 samples increases throughput of phospho flow. (a) Efficient barcoding of 36 samples. U937 cells were left untreated or were stimulated with IFN-γ (10 ng/ml) for 10 min. Unstimulated and stimulated samples were added to a 96-well plate in an alternating pattern across each row and down each column and labeled with six concentrations of Pacific Blue-NHS (0, 0.15, 0.6, 2.5, 10 or 40 μg/ml) and/or Alexa 488-NHS (0, 0.07, 0.3, 1.3, 5 or 20 μg/ml). Forward deconvolution of the last column (cells labeled with 40 μg/ml Pacific Blue-NHS) showed the expected pattern of high and low levels of Stat1 phosphorylation. Reverse deconvolution (bottom panel) of all stimulated or unstimulated cells produced the expected checkerboard pattern. (b) Miniature drug screen and titration of inhibitors with FCB. U937 cells were treated with various drugs before stimulation with IFN-γ, IL-6 and GM-CSF (stimulation). WHI-P154 (WHI; 50 μM), PD98059 (PD; 20 μM), Jak inhibitor I (Jak-1; 5 μM), and wortmannin (Wort; 2 μM) were added to the cells 30 min before stimulation; samples were barcoded with Pacific Blue-NHS and simultaneously stained with pStat1 Alexa 488, pStat3 PE and pStat5 Alexa 647 (left three plots). Jak inhibitor I was added at 0.005, 0.05, 0.5 or 5 μM for 30 min before stimulation (middle). WHI-P154 was added at 0.1, 1, 10 or 100 μM for 30 min before stimulation (right). Non-drug-treated positive and negative controls are included within each FCB staining set, allowing for internal normalization of each staining cocktail.

Figure 5:
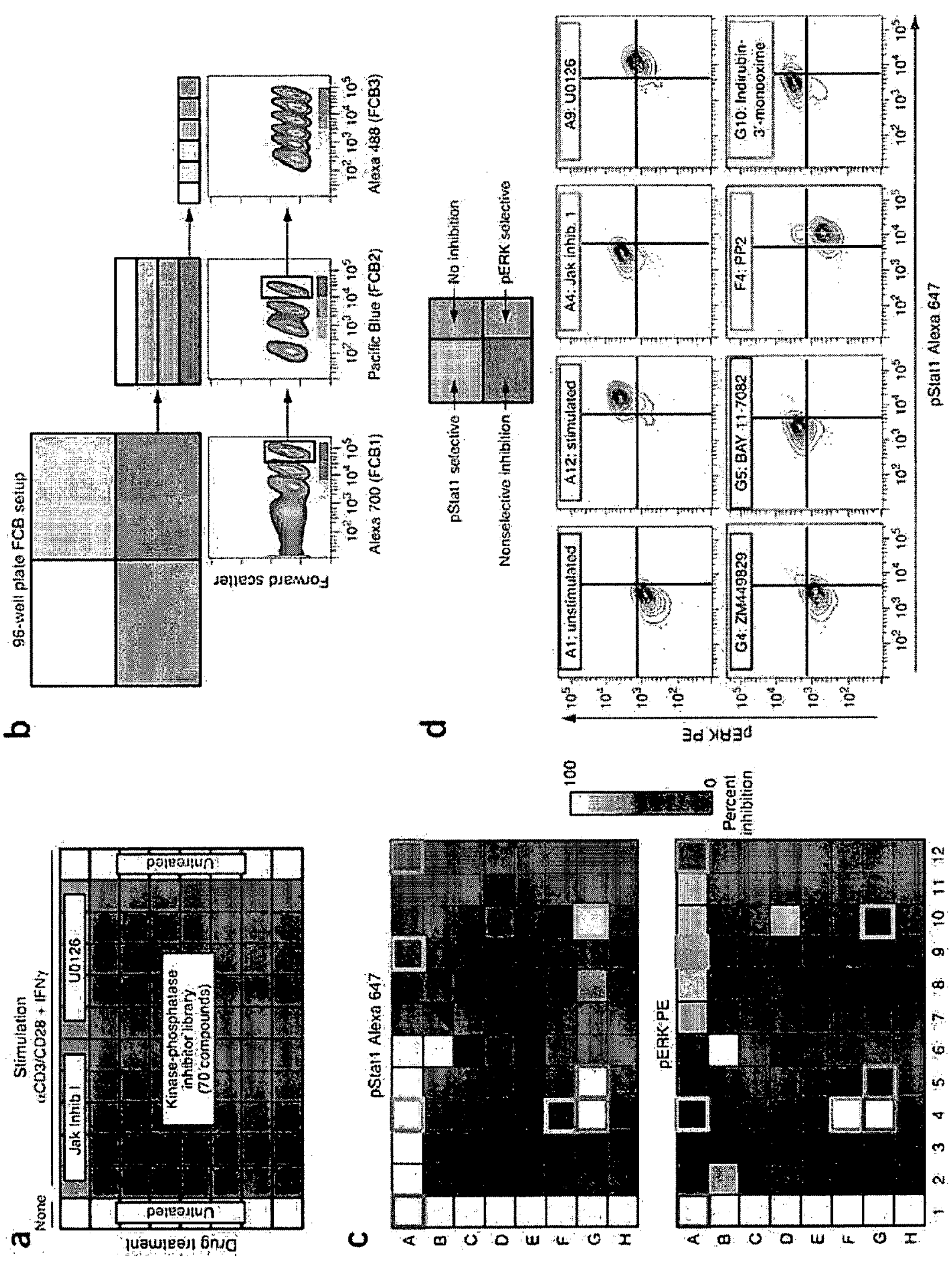

FIG. 5. Use of FCB in drug screening platforms. Small-molecule drug screening in 96-well plate format reveals selective inhibitors. (a) Layout of screening experiment. Jurkat cells were treated with 70 known small-molecule kinase or phosphatase inhibitors (20 μM), Jak inhibitor I (2 μM) or U0126 (20 μM) for 45 min before stimulation with 5 μg/ml anti-CD3 and anti-CD28 and 10 ng/ml IFN-γ for 5 min. (b) FCB setup for barcoding of 96-well plate. After fixation, cells were barcoded with Alexa 700-NHS (0, 0.06, 0.25 or 1 μg/ml) to delineate the four quadrants of the 96-well plate. Each quadrant was subdivided into four rows labeled with Pacific Blue-NHS (0, 0.04, 0.2 or 1 μg/ml) and six columns labeled with Alexa 488-NHS (0, 0.02, 0.06, 0.18, 0.5 or 1.5 μg/ml). Shown are pseudocolor FACS plots of the actual gating scheme used to deconvolute the samples in quadrant 4, row D (bottom right six samples in the plate). (c) Heat map representation of percent inhibition of ERK and Stat1 phosphorylation. Average fold change upon stimulation was 5.8 for pStat1 and 4.5 for pERK. Wells with black triangles were excluded from the analysis due to high fluorescence of the drug in the phospho-protein fluorescence channels. Colored squares are drawn over wells analyzed in d. (d) Two-dimensional plots of pERK versus pStat1. The colored hypothetical plot shows four quadrants representing nonselective inhibitors (and unstimulated controls) in red, stimulated controls in green, and pStat1 or pERK selective inhibitors in orange.

Figure 6:
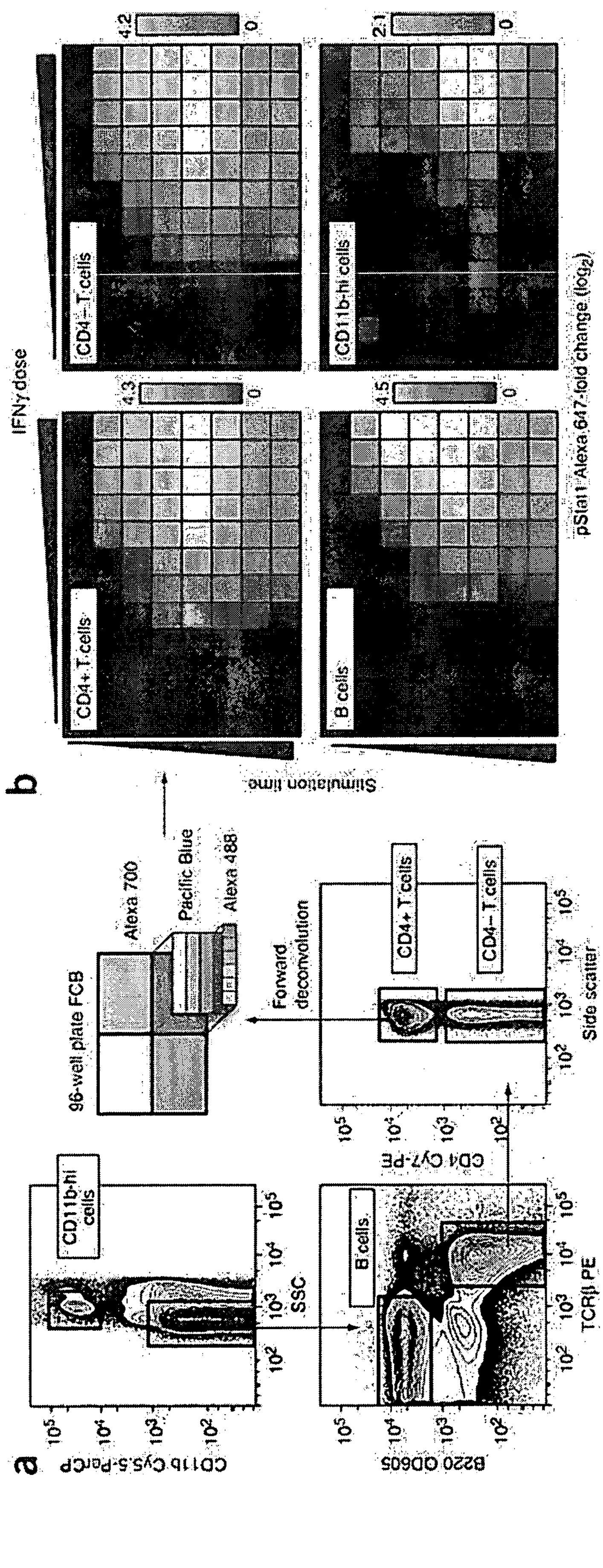

FIG. 6. Use of FCB to label primary cell populations. Signaling profiling in complex heterogeneous populations reveals thermodynamic and kinetic differences in responses to IFN-γ stimulation. (a) Mouse splenocytes were stimulated with different concentrations of IFN-γ across each row (0, 0.17, 0.5, 1.5, 4.5, 13, 40, 120, 370, 1,100, 3,300 or 10,000 pg/ml) for 0, 4, 8, 15, 30, 60, 120 or 180 min (each row representing a different time point). Cells were barcoded with three FCB markers (Alexa 700, Alexa 488 and Pacific Blue as in FIG. 5) during permeabilization, and stained with CD11b Cy5.5PerCP, B220 QD605, TCR PE, CD4 Cy7PE and pStat1 Alexa 647. Cell types were first gated based on surface markers to obtain CD11b-hi cells (neutrophils), B cells, CD4+ T cells and CD4-T cells. Each cell type was then deconvoluted to obtain the original 96-well plate layout. (b) Heat map representation showing the fold change in pStat1 levels on a log 2 scale across dose (from left to right) and time gradients (top to bottom). Yellow represents maximal induction, red indicates half-maximal induction, and black indicates no induction. Note that the scale for each cell type is different owing to different maximal induction of Stat1 phosphorylation.

Figure 7:
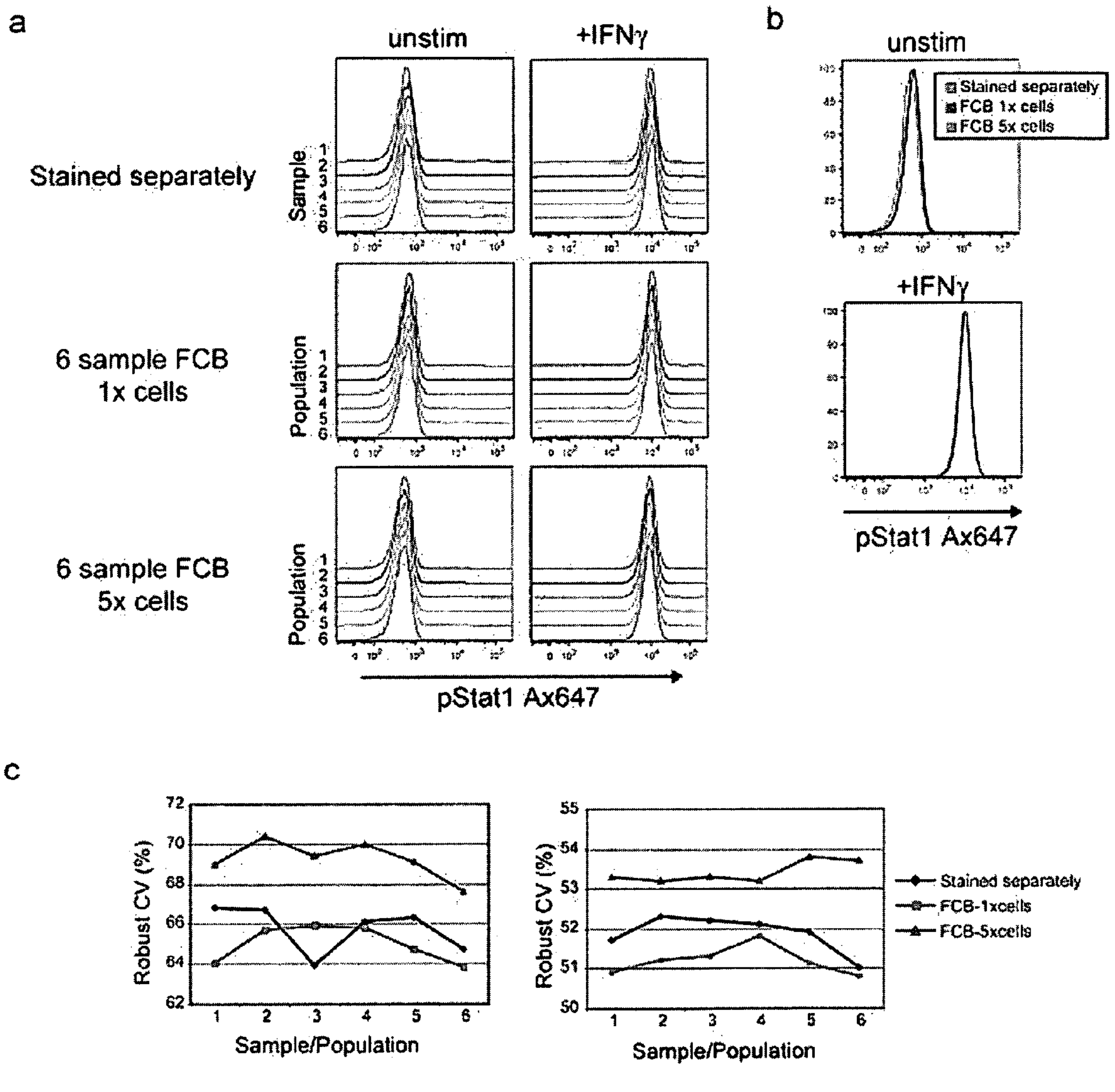

FIG. 7. Increasing cell number to antibody ratio does not significantly impact phospho antibody staining. a) U937 cells were left unstimulated or stimulated with 10 ng/ml of IFN-γ for 10 minutes. The samples were fixed with formaldehyde and permeabilized with methanol. At this stage, the samples were placed in a 96 well plate, and either left untreated, or were labeled with 6 concentrations of PacBlu. Non-PacBlu treated samples were stained separately to generate 6 stained samples. The PacBlu barcoded samples were combined at two different cell concentrations and stained. These samples contained either the same amount of total cells as each of the separately stained samples (1×=one million cells), or five times the amount of cells (5×=five million cells). All samples were stained with the same amount of pStat1 Ax647. b) One separately stained sample compared to the barcoded samples (all six populations are shown as one histogram) for the unstimulated and stimulated states. Note the nearly identical staining intensities. c) Plot of CV versus sample or population. The CV was measured on the Ax647 channel for each of the separately stained samples or for the 6 barcoded populations in the FCB samples.

Figure 8:
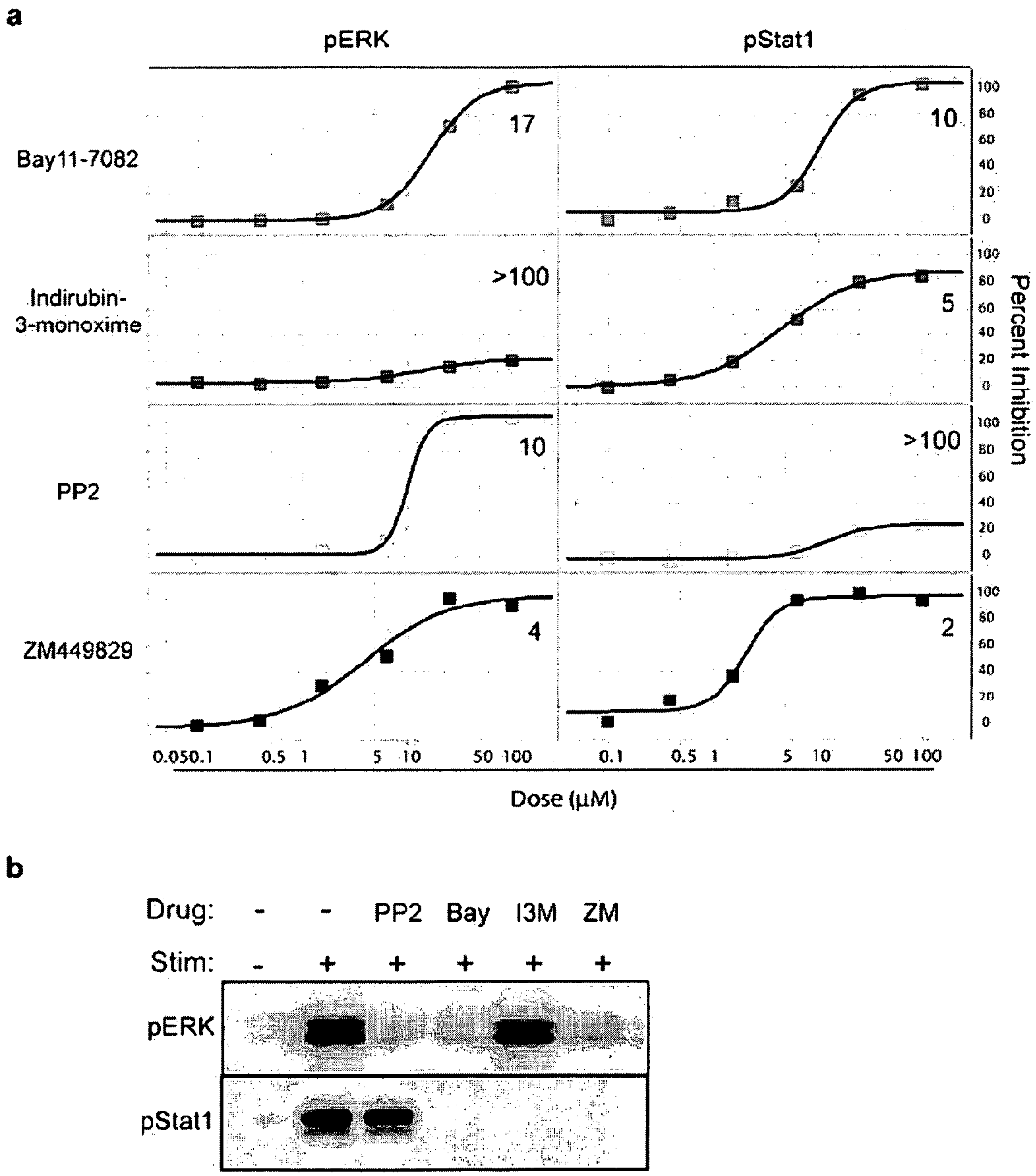

FIG. 8. Detailed titration of four hits from Jurkat drug screening experiment (FIG. 5). a) Four compounds: Bay11-7082, Indirubin-3-monoxime, PP2, and ZM449829 were added to Jurkat cells at different concentrations for 30 min prior to stimulation with IFN-γ (10 ng/ml) and anti-CD3/28 (5 μg/ml each). The cells were fixed and permeabilized, then stained with pStat1 Ax647 and pERK Ax488 antibodies. Percent inhibition of phosphorylation was plotted against concentration of drugs and fitted with a logistic regression curve to obtain IC50 values. Numbers in the top right of each plot are the IC50 value in μM units. b) Lysates were prepared from the same cells used for phospho flow and analyzed by western blot with pStat1 and pERK antibodies. Drugs were applied at 20 μM (same concentration as initial screen) for western blot analysis.

Figure 9:
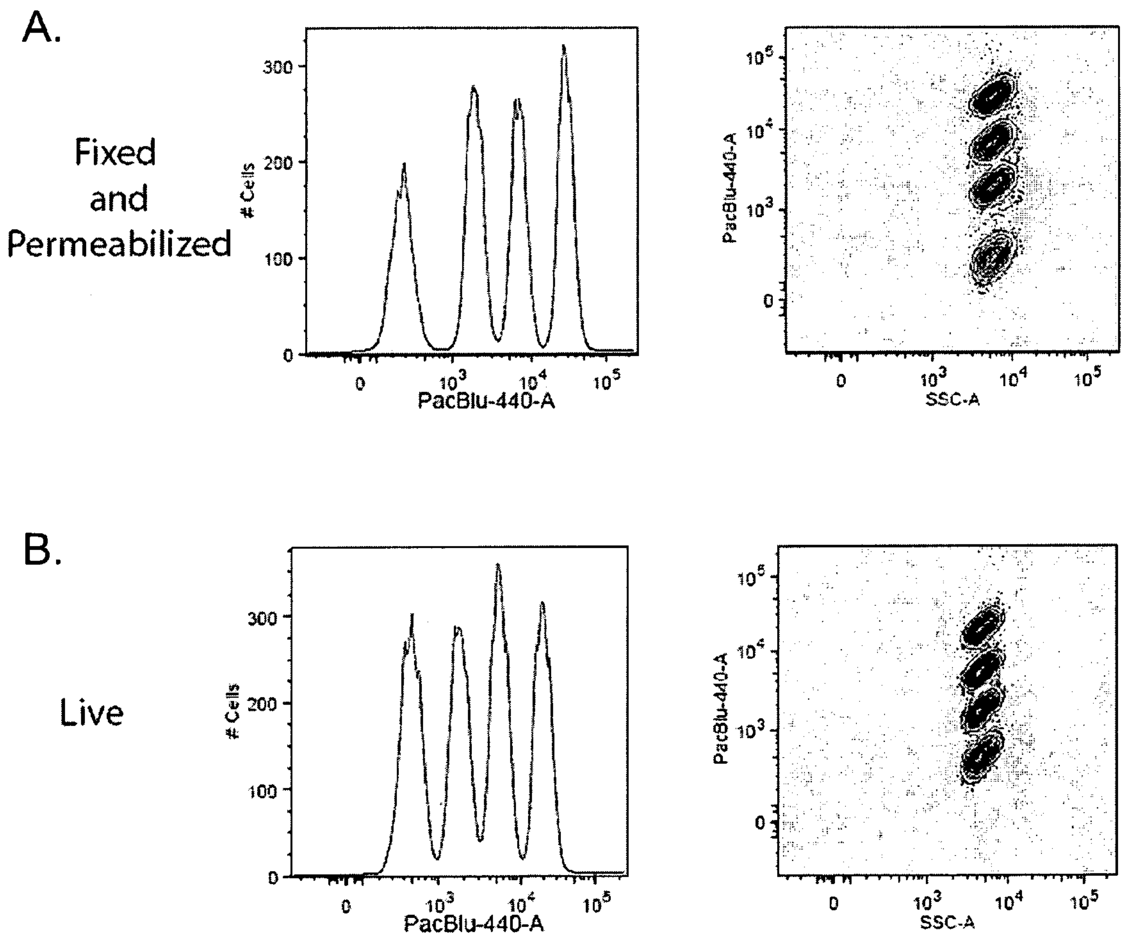

FIG. 9. FCB markers can be applied at different stages of flow cytometry staining experiments while cells are alive, fixed, and/or fixed and permeabilized. (A) U937 cells were fixed with formaldehyde and permeabilized with methanol containing 0, 0.125, 0.5, or 2 μg/ml Pacific Blue-NHS, and incubated for 15 min at room temperature. The cells were washed twice, then combined and analyzed on a LSR2. (B) Live U937 cells were treated with 0, 0.125, 0.5, or 2 μg/ml Pacific Blue-NHS, then washed twice and combined prior to analysis on an LSR2.

DEFINITIONS

As used herein, the term "antibody" refers to a protein consisting of one or more polypeptides substantially encoded by all or part of the recognized immunoglobulin genes. The recognized immunoglobulin genes, for example in humans, include the kappa (κ), lambda (l), and heavy chain genetic loci, which together comprise the myriad variable region genes, and the constant region genes mu (μ), delta (δ), gamma (γ), sigma (ϵ), and alpha (α) which encode the IgM, IgD, IgG, IgE, and IgA isotypes respectively. Antibody herein is meant to include full length antibodies and antibody fragments, and may refer to a natural antibody from any organism, an engineered antibody, or an antibody generated recombinantly for experimental, therapeutic, or other purposes as further defined below. Antibody fragments are known in the art and include, but are not limited to, Fab, Fab', F(ab')2, Fv, scFv, or other antigen-binding subsequences of antibodies, either produced by the modification of whole antibodies or those synthesized de novo using recombinant DNA technologies. Antibodies may be monoclonal or polyclonal and may have other specific activities on cells (e.g., antagonists, agonists, neutralizing, inhibitory, or stimulatory antibodies).

As used herein, the term "activation state-specific antibody" or "activation state antibody" or grammatical equivalents thereof, refer to an antibody that specifically binds to a corresponding and specific antigen. In certain embodiments, the corresponding and specific antigen is a specific isoform of an activatable protein. In certain embodiments, the binding of the activation state-specific antibody is indicative of a specific activation state of a specific activatable protein. Thus, in certain embodiments, the binding of an activation state-specific antibody to a corresponding isoform of an activatable protein is indicative of the identity of the activatable protein and of the activation state of the activatable protein. A number of antibodies, many of which are commercially available (for example, see Cell Signaling Technology, www.cellsignal.com, the contents which are incorporated herein by reference). have been produced which specifically bind to the phosphorylated isoform of a protein but do not specifically bind to a non-phosphorylated isoform of a protein. Many such antibodies have been produced for the study of signal transducing proteins which are reversibly phosphorylated. Non-limiting examples of such antibodies that find use in the present invention include: phospho-AKT Ser473 monoclonal anti-4E2, phospho-p44/42 MAP kinase (Thr202/Tyr204) monoclonal antibody, phospho-TYK2 (Tyr1054/1055) antibody, phospho-p38 MAP kinase (Thr180/Tyr182) monoclonal antibody 28B10, phospho-PKC-PAN substrate antibody, phospho-PKA-substrate, phospho-SAPK/JNK (Thr183/Tyr185) G9 monoclonal antibody, phospho-tyrosine monoclonal antibody (P-tyr-100), p44/42 MAPK, p38 MAPK, JNK/SAPK, phospho-AKT-Thr308, Stat1 (pY701), Stat3 (pY705), Stat5 (pY694), Stat6 (pY641), and ERK1/2 (pT202/pY204).

As used herein, an "activatable protein" or "substrate" or "substrate protein" or "protein substrate" grammatical equivalents thereof, refers to a protein that has at least one isoform (and in some cases two or more isoforms) that corresponds to a specific form of the protein having a particular biological, biochemical, or physical property, e.g., an enzymatic activity, a modification (e.g., post-translational modification), or a conformation. The activable protein can be activated or nonactivated with respect to a particular biological activity, modification, or conformation. Specifically, the "activated" or "active" form of the activatable protein has the particular biological activity, modification, or conformation, whereas the "non-activated" or "non-active" form of the activatable protein does not have (or has a lesser or diminished level of) the particular biological activity, modification, or conformation, respectively. In some embodiments, there may be more than one isoform associated with activity or activation state; for example, there may be an isoform associated with an "open" conformation available for substrate binding, a second "transition state" isoform, and an isoform devoid of activity (e.g., where the activity is inhibited). Examples of activatable proteins include, but are not limited to, phosphoproteins and phospho-lipids. Further examples of activatable proteins include, but are not limited to, kinases, phosphatases, PIP2, PIP3, G-proteins, G-protein coupled receptors (GPCRs), and proteases such as cysteine and serine proteases, including, but not limited to caspases, cathepsins and a variety of well known serine proteases.

As used herein, an "isoform" or grammatical equivalents thereof, refers to a form of an activatable protein having a specific, biological activity, modification, or conformation. The isoform can be an activated (or active) form, or non-activated (or not active) form of an activatable protein. As mentioned, in certain embodiments, the binding of an activation state-specific antibody to a corresponding isoform of an activable protein is indicative of the identity of the activatable protein and of the activation state of the activatable protein.

By "fluorescent label" is meant any molecule that may be detected via its inherent fluorescent properties. Suitable fluorescent labels include, but are not limited to, Pacific Blue, Pacific Orange, Alexa Fluor dyes (eg. Alexa 350, 430, 488, 555, 647, 700, and 750), fluorescein, rhodamine, tetramethylrhodamine, eosin, erythrosin, coumarin, methyl-coumarins, pyrene, Malacite green, stilbene, Lucifer Yellow, Cascade Blue™, Texas Red, IAEDANS, EDANS, BODIPY FL, LC Red 640, Cy 5, Cy 5.5, Cy7, LC Red 705 and Oregon green. Suitable optical dyes are described in the 1996 Molecular Probes Handbook by Richard P. Haugland, hereby expressly incorporated by reference. Suitable fluorescent labels also include, but are not limited to, green fluorescent protein (GFP; Chalfie, et al., Science 263(5148):802-805 (Feb. 11, 1994); and EGFP; Clontech-Genbank Accession Number U55762), blue fluorescent protein (BFP; 1. Quantum Biotechnologies, Inc. 1801 de Maisonneuve Blvd. West, 8th Floor, Montreal (Quebec) Canada H3H 1J9; 2. Stauber, R. H. Biotechniques 24(3):462-471 (1998); 3. Heim, R. and Tsien, R. Y. Curr. Biol. 6:178-182 (1996)), enhanced yellow fluorescent protein (EYFP; 1. Clontech Laboratories, Inc., 1020 East Meadow Circle, Palo Alto, Calif. 94303), luciferase (Ichiki, et al., J. Immunol. 150(12):5408-5417 (1993)), .beta.-galactosidase (Nolan, et al., Proc Natl Acad Sci USA 85(8): 2603-2607 (April 1988)) and *Renilla* WO 92/15673; WO 95/07463; WO 98/14605; WO 98/26277; WO 99/49019; U.S. Pat. No. 5,292,658; U.S. Pat. No. 5,418,155; U.S. Pat. No. 5,683,888; U.S. Pat. No. 5,741,668; U.S. Pat. No. 5,777,079; U.S. Pat. No. 5,804,387; U.S. Pat. No. 5,874,304; U.S. Pat. No. 5,876,995; and U.S. Pat. No. 5,925,558). All of the above-cited references are expressly incorporated herein by reference.

In certain embodiments, labels for use in the present invention include: Alexa-Fluor dyes (Alexa Fluor 350, Alexa Fluor 430, Alexa Fluor 488, Alexa Fluor 546, Alexa Fluor 555, Alexa Fluor 568, Alexa Fluor 594, Alexa Fluor 633, Alexa Fluor 647, Alexa Fluor 660, Alexa Fluor 680, Alexa Fluor 700, Alexa Fluor 750), Pacific Blue, Pacific Orange, Cascade Blue, Cascade Yellow and R-phycoerythrin (PE) (Molecular Probes) (Eugene, Oreg.), FITC, Rhodamine, and Texas Red (Pierce, Rockford, Ill.), Cy5, Cy5.5, Cy7 (Amersham Life Science, Pittsburgh, Pa.). Tandem conjugate protocols for Cy5PE, Cy5.5PE, Cy7PE, Cy5.5APC, Cy7APC can be found at www(dot)drmr(dot)com/abcon.

As used herein, "detectable cell barcode marker" or "DCB marker" or "DCB label", or grammatical equivalents thereof, is meant a moiety that can label a cell upon contact in a suitable buffer, either covalently or non-covalently. In certain embodiments, a DCB marker is functionalized to bind irreversibly to a cell, e.g., by having a reactive moiety thereon that forms a covalent bond with molecules present in or on cellular components (e.g., amine or thiol groups on proteins). Examples of amine-reactive DCB markers include, but are not limited to, Alexa Fluor succinimidyl esters (NHS) (Alexa 488-NHS, Alexa 700-NHS and Alexa 750-NHS) and Pacific Blue succinimidyl ester (Pacific Blue-NHS) from Molecular Probes. In certain embodiments, a DCB marker is functionalized to bind reversibly to a cell, e.g., attached to an antibody that binds to an antigen on/in a cell. Types of detectable characteristics for DCB labels/markers include, but are not limited to, fluorescence emission, molecular mass, catalytic activity, or other detectable characteristic. Virtually any distinct characteristic of a DCB label that is detectable (e.g., by flow cytometry, mass spectrometry, etc.) by can be used.

By "uniquely labeled", "distinctly labeled", "differentially labeled" or grammatical equivalents thereof is meant that a first label can be distinguished from a second label (or all other labels) in a detection assay either by its detection characteristic (e.g., emission wavelength, molecular mass) or its intensity/concentration/absolute amount.

As used herein, the term "determining" means to identify, i.e., establishing, ascertaining, evaluating, detecting or measuring, a value for a particular parameter of interest, e.g., a fluorescence parameter. The determination of the value may be qualitative (e.g., presence or absence) or quantitative, where a quantitative determination may be either relative (i.e., a value whose units are relative to a control (i.e., reference value) or absolute (e.g., where a number of actual molecules is determined).

By "candidate bioactive agent", "candidate agent", "candidate modulator", "candidate modulating agent", or "exogeneous compound" or grammatical equivalents herein is meant any molecule, e.g., protein, small organic molecule, carbohydrates (including polysaccharides), polynucleotide, lipids, etc. Generally a plurality of assay mixtures can be run in parallel with different agent concentrations to obtain a differential response to the various concentrations. Typically, one of these concentrations can serve as a negative control, i.e., at zero concentration or below the level of detection. In addition, positive controls can be used.

Candidate agents encompass numerous chemical classes. In certain embodiments, the candidate agents are small molecules. In certain embodiments, candidate agents are organic molecules, including small organic molecules, comprising functional groups necessary for structural interaction with proteins, e.g., hydrogen bonding, and may include one or more amine, carbonyl, hydroxyl or carboxyl group. The candidate agents may comprise cyclical carbon or heterocyclic structures and/or aromatic or polyaromatic structures substituted with one or more chemical functional groups.

Candidate agents can be obtained from a wide variety of sources, as will be appreciated by those in the art, including libraries of synthetic or natural compounds. As will be appreciated by those in the art, the present invention provides a rapid and easy method for screening any library of candidate modulators, including the wide variety of known combinatorial chemistry-type libraries.

The phrase "nucleic acid sequence encoding" or "gene encoding" refers to a nucleic acid that directs the expression of a specific protein or peptide. The nucleic acid sequences include both the DNA strand sequence that is transcribed into RNA and the RNA sequence that is translated into protein. The nucleic acid sequences include both the full-length nucleic acid sequences as well as non-full length sequences derived from the full-length protein. It being further understood that the sequence includes the degenerate codons of the native sequence or sequences, which may be introduced to provide codon preference in a specific host cell.

Where a recombinant microorganism or cell culture is described as hosting an "expression vector," this includes both extrachromosomal circular DNA and DNA that has been incorporated into the host chromosome(s). Where a vector is being maintained by a host cell, the vector may either be stably replicated by the cells during mitosis as an autonomous structure, or is incorporated within the host's genome.

The term "gene" as used herein is intended to refer to a nucleic acid sequence, which encodes a polypeptide. This definition includes various sequence polymorphisms, mutations, and/or sequence variants wherein such alterations do not affect the function of the gene product. The term "gene" is intended to include not only coding sequences but also regulatory regions such as promoters, enhancers, and termination regions. The term further includes all introns and other DNA sequences spliced from the mRNA transcript, along with variants resulting from alternative splice sites.

The term "nucleic acid" includes DNA, RNA (double-stranded or single stranded), analogs (e.g., PNA or LNA molecules) and derivatives thereof. The terms "ribonucleic acid" and "RNA" as used herein mean a polymer composed of ribonucleotides. The terms "deoxyribonucleic acid" and "DNA" as used herein mean a polymer composed of deoxyribonucleotides. The term "mRNA" means messenger RNA. An "oligonucleotide" generally refers to a nucleotide multimer of about 10 to 100 nucleotides in length, while a "polynucleotide" includes a nucleotide multimer having any number of nucleotides. As such, the term "nucleic acid" includes polymers in which the conventional backbone of a polynucleotide has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides.

As used herein, the term "protein" means at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration. In certain embodiments, the amino acids are in the (S) or L-configuration. If non-naturally occurring side chains are used, non-amino acid substituents may be used, for example to prevent or retard in vivo degradation. Proteins including non-naturally occurring amino acids may be synthesized or in some cases, made recombinantly; see van Hest et al., FEBS Lett 428:(1-2) 68-70 May 22, 1998 and Tang et al., Abstr. Pap Am. Chem. S218: U138 Part 2 Aug. 22, 1999, both of which are expressly incorporated by reference herein.

DETAILED DESCRIPTION OF THE INVENTION

As summarized above, the present invention is drawn to multiplex cellular assays that employ Detectable Cell Barcodes (DCB). In certain embodiments, different cell samples are labeled with different intensities/amounts of a DCB marker by treatment with different concentrations of an DCB label that binds to a cell (e.g., a cell-reactive form of a fluorophore or an antibody tagged with a molecular mass marker). This gives each sample a unique DCB signature. In certain embodiments, cell samples are coded with more than one type of DCB marker (e.g., DCB markers having distinct detection characteristics). In these embodiments, the number of different DCB signatures available increases geometrically because of multiplexing of DCB intensity with DCB detection characteristic (for example, using different channels on the flow cytometer).

For example, in flow cytometric embodiments employing FCB labels, an average of 6 different intensities for each FCB marker employed can be detected (although more is possible). Using multiple FCB labels in a combinatorial fashion allows bar coding of up to 36 samples with two FCB labels, up to about 216 samples with three FCB labels, up to about 1,296 samples with four FCB labels, and so on. Given the increasing number of fluorescent markers having distinct detection characteristics (e.g., fluorescent emission wavelengths) as well as flow cytometers that can detect them simultaneously, many thousands of distinct cell samples or more can be FCB labeled and analyzed in a single sample using the methods and compositions of the present invention.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits ranges excluding either or both of those included limits are also included in the invention.

Unless defined otherwise, all technical and scientific terms used herein have the same meaning as commonly understood to one of ordinary skill in the art to which this invention belongs. Methods recited herein may be carried out in any order of the recited events that is logically possible, as well as the recited order of events.

All patents and other references cited in this application are incorporated into this application by reference except insofar as they may conflict with those of the present application (in which case the present application prevails). The citation of any publication is for its disclosure prior to the filing date and should not be construed as an admission that the present invention is not entitled to antedate such publication by virtue of prior invention.

I. Methods of Detectable Cell Barcoding (DCB)

As summarized above, the present invention provides methods for multiplex cell analysis using DCB. By "multiplex" is meant that the multiple cell samples being analyzed are combined, e.g., into a single reaction tube, prior to analysis.

In certain embodiments, the methods of the invention are drawn to multiplex analysis of DCB labeled cells for a detectable characteristic of interest. In certain embodiments, a detectable characteristic is detectable in a flow cytometric assay, whereas in other embodiments a detectable characteristic is detectable using another detection system, e.g., a mass spectrometer. Detectable characteristics include, but are not limited to, fluorescence, physical characteristics, the presence of an analyte, cell number or frequency), etc. Virtually any characteristic that is detectable can be assayed for in the cells using the methods of the invention.

In certain embodiments, the detectable characteristic is the presence of one or more analytes in or on the cells (e.g., the presence of a cell surface marker).

In certain embodiments, the method includes the following steps.

a) Labeling the cells in each of the multiple cell samples with a unique DCB marker (or label) to produce multiple DCB-labeled cell samples. The DCB employed for each of the multiple cell samples are distinguishable from each other based on one or both of: i) detection characteristic of the DCB marker; and/or ii) intensity of the DCB marker. As such, cells from a particular cell sample will have a distinct DCB.

b) Combining the multiple DCB-labeled cell samples into a combined cell sample.

c) Analyzing the combined cell sample to detect the DCB and a detectable characteristic of interest of each cell.

e) Deconvoluting the result of the analyzing step such that the presence of the detectable characteristic for cells from each of the multiple cell samples is determined.

Certain aspects and embodiments of the methods of the invention are described in more detail below.

Cell Samples

The methods of the invention can be employed to analyze virtually any type of cell, including prokaryotic and eukaryotic cells.

Suitable prokaryotic cells include, but are not limited to, bacteria such as *E. coli*, various *Bacillus* species, and the extremophile bacteria such as thermophiles, etc.

Suitable eukaryotic cells include, but are not limited to, fungi such as yeast and filamentous fungi, including species of *Aspergillus, Trichoderma*, and *Neurospora*; plant cells including those of corn, sorghum, tobacco, canola, soybean, cotton, tomato, potato, alfalfa, sunflower, etc.; and animal cells, including fish, birds and mammals. Suitable fish cells include, but are not limited to, those from species of salmon, trout, tulapia, tuna, carp, flounder, halibut, swordfish, cod and zebrafish. Suitable bird cells include, but are not limited to, those of chickens, ducks, quail, pheasants and turkeys, and other jungle foul or game birds. Suitable mammalian cells include, but are not limited to, cells from horses, cows, buffalo, deer, sheep, rabbits, rodents such as mice, rats, hamsters and guinea pigs, goats, pigs, primates, marine mammals including dolphins and whales, as well as cell lines, such as human cell lines of any tissue or stem cell type, and stem cells, including pluripotent and non-pluripotent, and non-human zygotes.

Suitable cells also include those cell types implicated in a wide variety of disease conditions, even while in a non-diseased state. Accordingly, suitable eukaryotic cell types include, but are not limited to, tumor cells of all types (e.g., melanoma, myeloid leukemia, carcinomas of the lung, breast, ovaries, colon, kidney, prostate, pancreas and testes), cardiomyocytes, dendritic cells, endothelial cells, epithelial cells, lymphocytes (T-cell and B cell), mast cells, eosinophils, vascular intimal cells, macrophages, natural killer cells, erythrocytes, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. In certain embodiments, the cells are primary disease state cells, such as primary tumor cells. Suitable cells also include known research cells, including, but not limited to, Jurkat T cells, NIH3T3 cells, CHO, COS, etc. See the ATCC cell line catalog, hereby expressly incorporated by reference.

In certain embodiments, the cells used in the present invention are taken from a subject. As used herein "subject" refers to both human and other animals as well as other organisms, such as experimental animals. Thus, the methods and compositions described herein are applicable to both human and veterinary applications. In certain embodiments the subject is a mammal, including embodiments in which the subject is a human patient either having (or suspected of having) a disease or pathological condition.

In certain embodiments, the cells being analyzed are enriched prior to DCB labeling (described in detail below). For example, if the cells of interest are white blood cells derived from a human subject, whole blood from the subject may be subjected to density gradient centrifugation to enrich for peripheral blood mononuclear cells (PBMCs, or white blood cells). Cells may be enriched using any convenient method known in the art, including fluorescence activated cell sorting (FACS), magnetically activated cell sorting (MACS), density gradient centrifugation and the like. Parameters employed for enriching certain cells from a mixed population include, but are not limited to, physical parameters (e.g., size, shape, density, etc.), in vitro growth characteristics (e.g., in response to specific nutrients in cell culture), and molecule expression (e.g., expression of cell surface proteins or carbohydrates, reporter molecules, e.g., green fluorescent protein, etc.).

In certain embodiments, the methods of the present invention are carried out on live cells which retain viability during the course of the assay. By "retain viability" is meant that a certain percentage of the cells remain alive at the conclusion of the assay, including from about 20% viable up to and including about 100% viable. In certain other embodiments, the methods of the present invention are carried out in such a manner as the cells are rendered non-viable during the course of the assay, e.g., the cells may be fixed, permeabilized, or otherwise maintained in buffers or under conditions in which the cells do not survive. Such parameters are generally dictated by the nature of the assay being performed as well as the reagents being employed.

FIG. 9 shows results from a comparison between the fluorescent-based DCB labeling (i.e., FCB labeling) of fixed and permeabilized cells (panel A) versus the FCB labeling of live cells (panel B) using the same FCB label (i.e., Pacific Blue-NHS). As is evident from this figure, the resolution of the four FCB populations is clearly distinct under both conditions.

Flow Cytometric-Detectable Cell Barcodes (FCB)

The description below details embodiments of the present invention that are drawn to Fluorescent Cell Barcodes (FCBs). However, such descriptions are not meant to be limiting, as other classes of Detectable Cell Barcodes (DCBs) may be used in conjunction with other detection systems, e.g., distinct DCB labels based on molecular mass markers that can be detected using mass spectrometry.

Certain embodiments of the present invention employ unique FCB labeling of multiple cell samples that are analyzed for a detectable characteristic of interest using multiplex flow cytometry.

Flow cytometers are well known analytical tools that enable the characterization of particles on the basis of light scatter and particle fluorescence. In a flow cytometer, particles are individually analyzed by exposing each particle to an excitation light, typically one or more lasers, and the light scattering and fluorescence properties of the particles are measured. Particles, such as molecules, analyte-bound beads, individual cells, or subcomponents thereof, typically are labeled with one or more spectrally distinct fluorescent dyes, and detection is carried out using a multiplicity of photodetectors, one for each distinct dye to be detected. Flow cytometers are commercially available from, for example, BD Biosciences (San Jose, Calif.).

To determine the sample origin of each cell of a multiplexed sample upon flow cytometric analysis, each starting cell sample is labeled with a distinct flow cytometric-detectable cell barcode (FCB) prior to combining them. In this way, the starting sample from which an analyzed cell is derived can be determined based on the unique FCB signature.

In certain embodiments, the unique feature of an FCB marker is its intensity. In these embodiments, the starting cell samples are contacted to a distinguishing amount (concentration) of an FCB label that binds to the cells in the sample. In certain embodiments, the FCB label binds to cells covalently whereas in other embodiments the FCB label binds to cells non-covalently. The amount of FCB label contacted to each sample is calibrated such that the resulting FCB intensity of the cells is directly related to the amount of label used (i.e., the more FCB label contacted to the cell, the higher the intensity of the detected FCB label). Therefore, when the multiplexed FCB labeled cells are processed and analyzed by flow cytometry, the intensity of the detected FCB marker can be used to determine to which starting cell sample the cell belongs.

Determining the specific dilutions of FCB marker (or markers) to employ in the method of the present invention is well within the skill of those in the art. In certain embodiments, an FCB dilution scheme is tested empirically prior to implementation. As noted above, for a dilution series of an FCB marker to function in the methods of the invention, it should allow for the categorization of FCB labeled cells into their respective starting samples based on the intensity of the FCB label upon flow cytometric analysis.

In certain embodiments, the FCB label is serially diluted prior to contacting to each of the multiple starting cell samples. Serial dilutions of FCB label include, but are not limited to, serial dilution series ranging from serial two-fold dilutions to serial 20-fold dilutions, including serial 3-fold, serial 4-fold, serial 5-fold, serial 6 fold, serial 10-fold, etc.

In certain embodiments, the FCB marker is diluted in a manner that is not a serial dilution. For example, the FCB marker may be diluted 10-fold from the first cell sample to the second, 5 fold from the second to the third, and 2 fold from the third to the fourth, etc. As noted above, the specific dilution scheme employed may be tested empirically prior to implementation.

In certain embodiments, the unique characteristics of an FCB label is its flow cytometric detection characteristic. In these embodiments, the starting cell samples are each contacted to an FCB marker that is distinguishable based on its detection channel, e.g., fluorescence channel, scatter channel, etc. For example, an FCB label may include a fluorescent moiety that has a unique emission wavelength as compared to FCB labels of other samples. The identity of FCB label contacted to each sample is calibrated such that the resulting FCB detection characteristic of the cells is directly related to the type of FCB label used. Therefore, when the multiplexed FCB labeled cells are detected by flow cytometry and analyzed, the detection characteristic(s) of each FCB marker can be used to determine to which starting cell sample each cell belongs.

Determining the specific types of FCB markers to employ in the method of the present invention is well within the skill of those in the art. In certain embodiments, specific combinations of FCB labels are tested empirically prior to implementation. As noted above, for an FCB marker to function in the methods of the invention, it should allow for the categorization of FCB labeled cells into their respective starting samples based on the detection characteristics of the FCB label (or labels) upon flow cytometric analysis.

In certain embodiments, the specific type of FCB label used to for each cell sample is selected such that the detection characteristic of each label does not interfere with the detection characteristic of any other FCB label (whether the FCB label is present on the same cell or is present on cells from another starting sample) upon flow cytometric analysis. Such parameters are routinely considered by those of skill in the art of multi-parameter flow cytometry. Parameters that may influence the choice of FCB label to employ include, but are not limited to, overlap of the FCB labels present in the multiplex sample (e.g., fluorescence emission overlap of distinct fluorescent FCB labels), overlap of the detection characteristics of the FCB labels with the detectable characteristic being assayed for in the cells (described below), excitation wavelength, fluorescence intensity, compensation of the flow cytometric data, and the detector channels available in the flow cytometer being used for analysis. The selection of detectable characteristics of a cell sample, including FCB signatures and detectable characteristic of interest of the cells, and appropriate corresponding detection channels is well known and within the ability of one of skill in the art of flow cytometry.

As mentioned, the choice of the detection channels will depend on the application and the instrumentation used. For example, for use in a flow cytometer in which two channels are used to detect FCB fluorescence and a third is used to detect fluorescence emission associated with the detectable characteristic being assayed for in the cells (e.g., fluorescence from a labeled analyte-specific antibody), it is advantageous to minimize the spillover (or overlap) of the FCB emissions into the detection channel for the detectable characteristic. Thus, the detection channels are selected such that the two channels used for detecting the FCB emission are spectrally separated from the analyte detection channel, within the constraints imposed by the instrument and dyes available. Again, the selection of compatible dyes and channels is well known and within the ability of one of skill in the art.

In certain embodiments, the unique signature of an FCB label are based on both type of detectable characteristic and the intensity thereof. In these embodiments, at least two detectably distinct FCB labels are contacted to each of the multiple cell samples in distinguishing amounts, thereby imparting a unique FCB signature on the cells of each sample. In these embodiments, the number of different FCB signatures available increases geometrically (as the number of FCB labels and intensities increase) because of multiplexing of intensity with detection characteristic.

By way of example, a single FCB label can provide for the FCB labeling of from 2 to about 7 different cell samples, depending on the specifics of the assay. Assuming that an average of 6 different intensities for each FCB label can be detected (although more is possible), using multiple FCB labels in a combinatorial fashion allows barcoding of up to 36 samples with two FCB labels, up to about 216 samples with three FCB labels, up to about 1,296 samples with four FCB labels, and so on.

Figure 1:
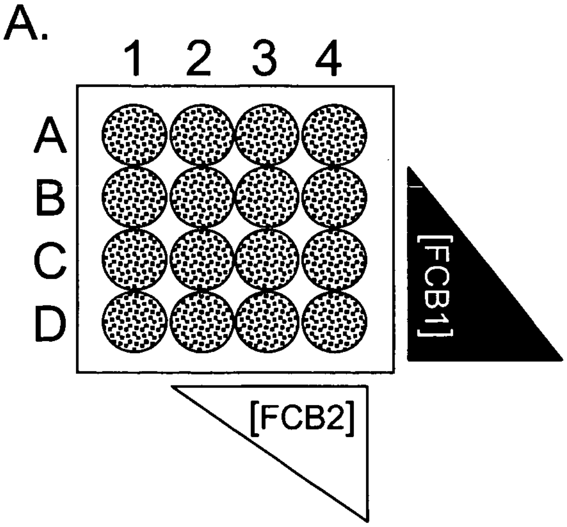
FIG. 1. Exemplary FCB (i.e., fluorescence-based detectable cell barcodes) labeling and detection. (A) FCB staining.

FIG. 1 provides an exemplary cell FCB stain and detection scheme. In panel A, 16 different cell samples are arrayed in a 4×4 culture plate and contacted to distinct concentrations of FCB1 and FCB2 labels (indicated in the bottom and right of the plate, where the depth of the triangle indicates the concentration of each label). Note that no FCB1 label is added to the cells in row A and no FCB2 label is added to the cells in column 1. As such, one distinguishing characteristic of an FCB label may be its absence. While not shown in this example, there are myriad ways to label cells with FCB markers such that each cell can be categorized upon multiplex analysis. Further, staining procedures can include one or more control samples (e.g., samples that should have identical FCB labels present in different wells as a staining control).

Once labeled with the FCB, the cells can be processed and prepared for multiplex analysis as desired (e.g., combined into a single reaction tube and contacted to an analyte specific antibody having a fluorescent label that is distinct from the FCB labels). After processing, the flow cytometric detectable characteristics of each of the cells in the single sample are determined. For each cell analyzed, the starting sample from which it is derived can be determined based on its FCB signature. Specifically, the intensity of both the FCB1 and FCB2 (including the absence of an FCB label) will indicate from which starting sample a cell was derived. For example, a cell having no detectable FCB1 marker (−) and the highest detectable FCB2 marker (+++) is from the cells in well A4 (as shown in panel A).

In certain embodiments, the FCB marker is a fluorescent dye. Fluorescent dyes (fluorophores) suitable for use as FCB markers in the present invention can be selected from any of the many dyes suitable for use in imaging applications, especially flow cytometry. A large number of dyes are commercially available from a variety of sources, such as, for example, Molecular Probes (Eugene, Oreg.) and Exciton (Dayton, Ohio), that provide great flexibility in selecting a set of FCB dyes having the desired spectral properties.

Examples of fluorophores from which suitable FCB markers can be selected include, but are not limited to, 4-acetamido-4'-isothiocyanatostilbene-2,2' disulfonic acid; acridine and derivatives such as acridine, acridine orange, acridine yellow, acridine red, and acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate (Lucifer Yellow VS); N-(4-amino-1-naphthyl)maleimide; anthranilamide; Brilliant Yellow; coumarin and derivatives such as coumarin, 7-amino-4-methylcoumarin (AMC, Coumarin 120), 7-amino-4-trifluoromethylcouluarin (Coumaran 151); cyanine and derivatives such as cyanosine, Cy3, Cy5, Cy5.5, and Cy7; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylaminocoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein isothiocyanate (FITC), fluorescein chlorotriazinyl, naphthofluorescein, and QFITC (XRITC); fluorescamine; IR144; IR1446; Lissamine™; Lissamine rhodamine, Lucifer yellow; Malachite Green isothiocyanate; 4-methylumbelliferone; ortho cresolphthalein; nitrotyrosine; pararosaniline; Nile Red; Oregon Green; Phenol Red; B-phycoerythrin;

o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), 4,7-dichlororhodamine lissamine, rhodamine B sulfonyl chloride, rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, and tetramethyl rhodamine isothiocyanate (TRITC); riboflavin; rosolic acid and terbium chelate derivatives; xanthene; Alexa-Fluor dyes (e.g., Alexa Fluor 350, Alexa Fluor 430, Alexa Fluor 488, Alexa Fluor 546, Alexa Fluor 555, Alexa Fluor 568, Alexa Fluor 594, Alexa Fluor 633, Alexa Fluor 647, Alexa Fluor 660, Alexa Fluor 680, Alexa Fluor 700, Alexa Fluor 750), Pacific Blue, Pacific Orange, Cascade Blue, Cascade Yellow; Quantum Dot dyes (Quantum Dot Corporation); Dylight dyes from Pierce (Rockford, Ill.), including Dylight 800, Dylight 680, Dylight 649, Dylight 633, Dylight 549, Dylight 488, Dylight 405; or combinations thereof. Other fluorophores or combinations thereof known to those skilled in the art may also be used, for example those available from Molecular Probes (Eugene, Oreg.) and Exciton (Dayton, Ohio).

Table 1 below provides a non-limiting list of fluorescent moieties that find use in the present invention along with their excitation and emission wavelengths. The fluorophores listed may be used as FCB markers (either alone or in combination) or as the fluorophore for the analyte specific binding agent. As indicated above, the specific fluorophore(s) employed in the methods of the invention will depend on the specific parameters of the assay, including the excitation and detection capabilities of the flow cytometer used.

TABLE 1

Excitation and Emission characteristics of exemplary fluorescent dyes.

| Flourophore | Excitation (nm) | Emission (nm) |
|---|---|---|
| Reactive Dyes | | |
| Hydroxycoumarin | 325 | 386 |
| Methoxycoumarin | 360 | 410 |
| Cascade Blue | 375; 400 | 423 |
| Aminocoumarin | 350 | 445 |
| Pacific Blue | 410 | 455 |
| BODIPY-FL | 503 | 512 |
| Fluorescein | 495 | 519 |
| FluorX | 494 | 520 |
| Lucifer yellow | 425 | 528 |
| NBD | 466 | 539 |
| Pacific Orange | 400 | 551 |
| TRITC | 547 | 572 |
| X-Rhodamine | 570 | 576 |
| R-Phycoerythrin (PE) | 480; 565 | 578 |
| Lissamine Rhodamine B | 570 | 590 |
| Red 613 | 480; 565 | 613 |
| Texas Red | 589 | 615 |
| Allophycocyanin (APC) | 650 | 660 |
| PE-Cy5 conjugates | 480; 565; 650 | 670 |
| PerCP | 490 | 675 |
| TruRed | 490, 675 | 695 |
| APC-Cy7 conjugates | 650; 755 | 767 |
| PE-Cy7 conjugates | 480; 565; 743 | 767 |
| Alexa Fluor Dyes (Molecular Probes) | | |
| Alexa Fluor 350 | 346 | 445 |
| Alexa Fluor 488 | 494 | 517 |
| Alexa Fluor 430 | 430 | 545 |
| Alexa Fluor 532 | 530 | 555 |
| Alexa Fluor 546 | 556 | 573 |

TABLE 1-continued

Excitation and Emission characteristics of exemplary fluorescent dyes.

| Flourophore | Excitation (nm) | Emission (nm) |
|---|---|---|
| Alexa Fluor 555 | 556 | 573 |
| Alexa Fluor 568 | 578 | 603 |
| Alexa Fluor 594 | 590 | 617 |
| Alexa Fluor 633 | 621 | 639 |
| Alexa Fluor 647 | 650 | 668 |
| Alexa Fluor 660 | 663 | 690 |
| Alexa Fluor 680 | 679 | 702 |
| Alexa Fluor 700 | 696 | 719 |
| Alexa Fluor 750 | 752 | 779 |
| Cy Dyes (AP Biotech) | | |
| Cy2 | 489 | 506 |
| Cy3 | (512); 550 | 570; (615) |
| Cy3.5 | 581 | 596; (640) |
| Cy5 | (625); 650 | 670 |
| Cy5.5 | 675 | 694 |
| Cy7 | 743 | 767 |
| Nucleic Acid Dyes | | |
| Acridine Orange | 503 | 530/640 |
| DAPI | 345 | 455 |
| Hoechst 33258 | 345 | 478 |
| SYTOX Blue | 431 | 480 |
| Hoechst 33342 | 343 | 483 |
| YOYO-1 | 491 | 509 |
| SYTOX Green | 504 | 523 |
| Thiazole Orange | 510 | 530 |
| TOTO-1 | 509 | 533 |
| TO-PRO-1 | | |
| SYTOX Orange | 547 | 570 |
| Chromomycin A3 | 445 | 575 |
| Mithramycin | 445 | 575 |
| Propidium Iodide (PI) | 536 | 617 |
| Ethidium Bromide | 493 | 620 |
| 7-AAD | 546 | 647 |
| TOTO-3 | 642 | 661 |
| TO-PRO-3 | | |
| LDS 751 | 543; 590 | 712; 607 |

Table 2 below provides exemplary combinations of fluorophores that may be used together in combinations of 2, 3 or 4 as FCB markers or as the fluorophore for the analyte specific binding agent. This table is by no means comprehensive. In Table 2, 20 different 2 dye combinations, 9 different 3 dye combinations, and 8 different 4 dye combinations are denoted (read vertically; filled-in black box indicates dyes in the combination).

TABLE 2

Exemplary Dye Combinations (AF = Alexa Fluor).

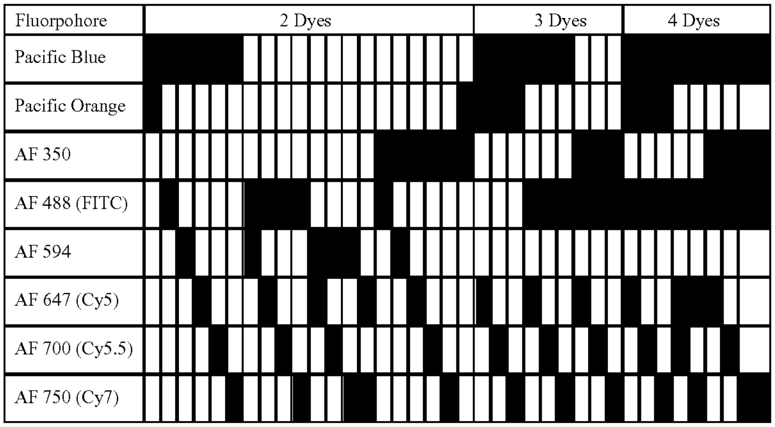

In certain embodiments, the fluorescent dyes employed as FCB markers are functionalized, meaning they contain a reactive group that promotes association (e.g., covalent attachment) with the cells being labeled. The functionalization of fluorescent labels with chemically reactive groups such as thiols, amines, carboxyls, etc. is generally known in the art. In certain embodiments, the reactive group is covalently attached to the fluorescent moiety, the covalent attachment being either direct or via a linker (e.g., a polymeric linker, including polyethylene glycol or PEG). A wide variety of functionalized fluorescent reagents are commercially available which contain functional groups, and thus may be used as FCB markers. Examples of such functionalized fluorescent reagents include, but are not limited to, fluorescent dyes conjugated to isothiocyanate groups, amino groups, haloacetyl groups, maleimides, succinimidyl esters, thiols, aldehyde, hydrazide, and sulfonyl halides, all of which may be used to covalently attach the fluorescent dye to a second molecule (e.g., a molecule in or on a cell, as is described herein).

In certain embodiments, an FCB label binds to a cell non-covalently. Examples of non-covalent association include interactions with cellular components such as DNA, RNA, lipids, membranes, organelles, etc. through hydrophobic, hydrogen-bonding, Van der Waals interactions, or other chemical interactions, etc. As such, any binding interaction between a cell and an FCB label may be used provided that it allows for marking of a cell for the duration of an FCB assay (i.e., until the FCB marker is detected by flow cytometric analysis).

In certain embodiments, labels employed as FCB markers are indirectly detected, that is, the moiety that is attached to the cell is not fluorescent, but rather is one partner of a binding pair. By "partner of a binding pair" is meant one of a first and a second moiety, wherein the first and the second moiety have a specific binding affinity for each other. Suitable binding pairs for use in the invention include, but are not limited to, antigens/antibodies (for example, digoxigenin/anti-digoxigenin, dinitrophenyl (DNP)/anti-DNP, dansyl-X-anti-dansyl, Fluorescein/anti-fluorescein, lucifer yellow/anti-lucifer yellow, and rhodamine anti-rhodamine), biotin/avidin (or biotin/streptavidin) and calmodulin binding protein (CBP)/calmodulin. Other suitable binding pairs include polypeptides such as the FLAG-peptide [Hopp et al., BioTechnology, 6:1204-1210 (1988)]; the KT3 epitope peptide [Martin et al., Science, 255:192-194 (1992)]; tubulin epitope peptide [Skinner et al., J. Biol. Chem., 266:15163-15166 (1991)]; and the T7 gene 10 protein peptide tag [Lutz-Freyermuth et al., Proc. Natl. Acad. Sci. USA, 87:6393-6397 (1990)] and the antibodies each thereto. In these embodiments, the FCB marker is used in the same manner as a directly detectable FCB marker. For example, if the intensity of the FCB marker is used as a parameter to distinguish the cells upon flow cytometric detection of the multiplex sample, the indirectly detectable FCB marker (e.g., functionalized biotin) is contacted to the cells at different concentrations, just as with directly detectable FCB markers. Subsequent contacting of the cells with the second, detectable binding partner (e.g., fluorescently labeled streptavidin, streptavidin-conjugated particle, etc.) will allow for categorization of the cells after detection of the flow cytometric characteristics characteristics of the cells.

As mentioned above, the cells being assayed in the FCB method described herein may be subjected to fixatives and/or permeabilization reagents, depending on certain parameters of the FCB assay being performed. For example, when employing FCB labels functionalized with thiol-reactive groups (e.g., maleimide) as one of the FCB markers, permeabilization of the cells may improve the efficiency of cell labeling, as this will allow access of the functionalized FCB label to the interior of the cells where the majority of the thiol groups are located (e.g., cysteine residues present in intracellular proteins). Fixation and/or permeabilization of cells can be achieved using any number of cross linking and permeabilizing reagents that are well known in the art, including, but not limited to, paraformaldehyde, glutaraldehyde, digitonin, saponin, triton, tween, methanol, ethanol, acetone (or other detergents and alcohols) and the like. Indeed, reagents and kits for permeabilization and fixation of cells for flow cytometric analysis are available from commercial vendors (e.g., CytoFix/CytoPerm buffer; PharMingen, La Jolla, Calif.).

The FCB marking of cells may be accomplished at any of a number of steps in the methods of the present invention that are prior to combining the cells into a single sample. For example, certain embodiments of the subject invention are drawn to multiplex drug screening assays in which a library of drugs is assayed in parallel to identify one which among them can inhibit a specific cellular process. For this example, we will assume that the readout for the assay is detection of an activated isoform of a signaling protein using an isoform-specific antibody (e.g., an antibody that binds to a specific phosphorylated isoform of the signaling protein of interest).

This example can be broken down into the following steps: 1) obtaining and plating the multiple cell samples (e.g., in a 96-well plate), 2) contacting each of the cell samples with a drug from the library, 3) initiating the cellular response of interest (e.g., adding an agonist), 4) stopping the reaction, 5) permeabilizing/fixing the cells, 6) washing the cells, 7) multiplexing (i.e., combining) the samples, and 8) performing the detection steps (e.g., contacting the permeabilized/fixed cells with the isoform specific antibody and detecting the fluorescence of the multiplexed sample using flow cytometry). In this example, each of the cell samples can be labeled with a distinct FCB at any of steps 1 to 6, but not thereafter (i.e., not after multiplexing the samples). As such, FCB marking of each cell sample can be done at any convenient stage of the assay prior to the multiplexing (i.e., combining) step.

In certain embodiments, the cells are pretreated with reagents that increase labeling efficiency. For example, to label cells with amine reactive FCB labels, such as succinimidyl esters, the labeling requires basic pH conditions, such as bicarbonate or other such buffer. This treatment promotes the presence of deprotonated and nucleophilic amine groups on lysine residues. Further, to label cells with large FCB labels (e.g., particles, large proteins such as PE, PerCP, or APC, which are typically prepared in thiol reactive forms), cells may need to be treated with a reducing agent such as DTT or TCEP to promote the reduction of disulfide bonds into individual thiol groups. These steps enhance the labeling efficiency of the FCB labels and reduce the amount that is necessary to obtain high labeling levels, cutting overall cost and improving consistency.

In certain embodiments, cells may need to be treated with quenching reagents that eliminate free, reactive FCB labeling moieties after the FCB labeling step. In certain embodiments, this can be achieved by adding free amines such as hydroxylamine, ethanolamine, etc., for amine reactive groups, or free thiols such as dithiothreitol (DTT), beta-mercaptoethanol, etc., for thiol reactive groups to the samples prior to combining. In this way, one avoids having reactive FCB labels remaining in the FCB labeled samples, thereby reducing the potential for inappropriate labeling of cells in later steps of the assay.

Detectable Characteristics

As summarized above, certain embodiments of the present invention include detection of a non-DCB detectable characteristic of the cells being assayed in the multiplex DCB assays of the invention. By "non-DCB detectable characteristic" is meant that the characteristic is detectable in the assay but not related to the DCB signature of the cell. Detectable characteristics include, but are not limited to, presence of an analyte, fluorescence emission, physical characteristic (e.g., size, shape, granularity, etc.), cell number (or frequency), etc. Virtually any detectable characteristic of interest can be assayed for as the detectable characteristic of interest.

In certain embodiments, the methods of the present invention are drawn to detecting the presence of an analyte associated with (e.g., in, on, or attached to) the cells being assayed, either qualitatively or quantitatively.

In certain of these embodiments, the method includes contacting the combined (or multiplexed) DCB-marked cell sample with a detectable analyte-specific binding agent. By "analyte-specific binding agent" and grammatical equivalents thereof, is meant any molecule, e.g., nucleic acids, small organic molecules, and proteins, nucleic acid binding dye (e.g., ethidium bromide) which are capable of associating with a specific analyte (or specific isoform of an analyte) in a cell over any others. Analytes of interest include any molecule associated with or present within the DCB marked cells being analyzed in the subject methods. As such, analytes of interest include, but are not limited to, proteins, carbohydrates, organelles, nucleic acids, infectious particles (e.g., viruses, bacteria, parasites), metabolites, etc.

In certain embodiments, the analyte-specific binding agent is a protein. In certain of these embodiments, the analyte-specific binding agent is an antibody, including an activation state-specific antibody. Accordingly, the methods and compositions of the present invention may be used to detect any particular element isoform in a sample that is antigenically detectable and antigenically distinguishable from other isoforms of the activatable element that are present in the sample. For example, the activation state-specific antibodies of the present invention can be used in the present methods to identify distinct signaling cascades of a subset or subpopulation of complex cell populations; and the ordering of protein activation (e.g., kinase activation) in potential signaling hierarchies.

In certain embodiments, the analyte-specific binding agent is a nucleic acid, where in certain embodiments the nucleic acid is specific for a gene (or gene product) of interest in the cells being analyzed (e.g., a nucleic acid probe specific for an mRNA of interest).

In certain embodiments, the analyte-specific binding agent is a fluorescent nucleic acid binding moiety, e.g., acridine orange, ethidium bromide, DAPI, LDS 750, and the like. Such binding agents find use in many flow cytometric applications, including determining the cell cycle status of a cell or as agents that mark cells that are undergoing apoptosis or are necrotic, as is known in the art.

In certain embodiments, multiple detectable analyte-specific binding agents are employed in an DCB method in accordance with the present invention. By "multiple analyte-specific binding agents" is meant that at least 2 or more analyte-specific binding agents are used, including 3 or more, 4 or more, 5 or more, etc. In certain embodiments, each of the different analyte-specific binding agents are labeled (again, either directly or indirectly) with a distinctly detectable label (e.g., fluorophores that have emission wavelengths that can be detected in distinct channels on a flow cytometer, with or without compensation; molecular mass labels have distinguishable masses that can be differentially detected by mass spectrometry). The multiple analyte-specific binding agents can bind to the same analyte in or on a cell (e.g., two antibodies that bind to different epitopes on the same protein), to different analytes in or on the cell, or in any combination (e.g., two agents that bind the same analyte and a third that binds to a distinct analyte). The upper limit for the number of analyte specific binding agents will depend largely on the parameters of the assay (e.g., the DCB labels used) and the detection capacity of the detecting system employed.

Data Analysis and Deconvolution

Analysis of the data acquired from a DCB multiplexed sample of the invention involves deconvolution. By "deconvolution" is meant a process, whether performed manually or in an automated system, by which the detected DCB of each cell is used to determine from which original sample it was derived. Because the type and amount of each DCB label for each of the starting samples is known, the detected DCB signature of each cell (i.e., its DCB signature) can be used to positively identify its sample of origin. Deconvolution of DCB multiplexed data can be done using any convenient method, including using computer-based analysis software known in the art (e.g., FlowJo and CellQuest software packages, available from TreeStar, Inc., and BD Biosciences, respectively). Deconvolution can be done manually (e.g., viewing the data and categorizing the cells by hand), automatically (e.g., by employing data analysis software configured specifically to deconvolute DCB data), or a combination thereof. In certain embodiments, computer programs can be employed to create individual data files for each of the deconvoluted DCB samples which correspond to the original starting samples for ease of data manipulation and/or interpretation. The Examples section below provides exemplary deconvolution procedures used in embodiments of the invention in which flow cytometry is employed as the analysis platform.

Analysis of the data acquired from a DCB multiplexed sample of the invention involves analyzing the cells for the detectable characteristic(s) of interest (as described in detail above). Analysis of the detectable characteristic may be done at any convenient step in the data analysis phase, including before, during or after deconvolution. Indeed, because the acquired data can be analyzed and re-analyzed at will, no limitation with regard to the order of deconvolution and analysis of the detectable characteristic(s) is intended.

II. Kits

The present invention provides kits that find use in performing the methods of the invention as described above. The embodiments of kits of the invention described below are meant to be exemplary and not limiting, as there are a variety of potential configurations that will allow one to practice the methods of the invention as described above.

In certain embodiments, kits of the invention include one or more DCB labels. In certain of these embodiments, the one or more DCB labels are reactive labels (e.g., amine reactive, thiol reactive, etc.) that are capable of covalently attaching to cells under appropriate reaction conditions. In certain embodiments, the DCB labels bind to cells through non-covalent interactions. The one or more DCB labels can be provided in the kit in any convenient form, including as dry reagents (e.g., lyophilized) or in a liquid buffer (e.g., as a suspension, dissolved, etc.).

In certain embodiments, the one or more DCB labels are provided in a form that facilitates DCB labeling of multiple cell samples. For example, each of the one or more DCB labels may be provided in an amount that is optimized for DCB labeling reactions. By "optimized for DCB labeling reactions" means that it is not necessary for the user to run preliminary DCB labeling experiments to determine the amount of the DCB label needed to differentially mark each cell sample.

Thus, in certain embodiments, each of the one or more DCB labels are provided in a single container (or tube) in which a dilution scheme (e.g., the serial dilution factor) that will allow differential labeling of multiple cell samples based on DCB intensity is known. This dilution scheme will be noted on the kit, e.g., on the label or as independent instructions.

In certain other embodiments, each of the one or more DCB labels is provided such that subsequent dilution by the user is not required (meaning they are pre-measured/diluted for the user). For example, in a kit for labeling multiple cell samples with a single type of DCB label, the kit may include four tubes of the DCB label, each of which contains a different amount that is know to label cells in an intensity-distinct manner. Kits having more than one DCB label may separately provide distinct amounts of each DCB label (e.g., provide four tubes having distinct amounts for each of the DCB labels) so that the user can employ them in any desired combination. In contrast, kits having more than one DCB label may include ready-made combinations of the different DCB labels so that the user does not need to combine them upon use. For example, a kit may provide 16 tubes having the desired combinations of 2 DCB labels, each of which have four distinct intensities (e.g., providing pre-combined samples to stain cells as shown in FIG. 1).

It is clear from the above description of the kits of the invention that a wide variety of kit configurations are possible with regard to the type and amount of DCB labels provided. Kits may therefore include anywhere from 1 to about 15 different types of DCB labels in optimized amounts and/or configurations (e.g., in separate, user combinable formats; in separate, pre-combined formats; or a combination of both).

In certain embodiments, the one or more DCB labels are provided in a convenient reaction vessel (or tube) that facilitates use by the end user. For example, the DCB labels/reagents may be provided in a multi-well strip format (e.g., including 4, 6, 8, 10, 12 or more wells) or multi-well plate format (e.g., including 4, 6, 12, 24, 48, 96, 192, 384 or more wells). Formats for providing DCB labels also include those configured for use with multi-channel pipettors and/or any of a number of robotic pipetting apparatuses.

For example, the one or more DCB labels can be provided in a multi-well strip having four wells where the first well contains the DCB label in a pre-optimized amount (or concentration). Upon use, the user simply dilutes the DCB label into the last three wells (e.g., using a specified dilution scheme) and then applies the DCB label(s) to the cell samples of interest as desired (or, alternatively, the cells may be added to the wells of the multi-well strip).

As another example, the kit may contain a multi-well plate (or strip) in which the DCB label(s) are pre-aliquoted into the wells in an optimized configuration. In this format, the end user merely contacts the cell samples of interest to the pre-loaded DCB labels (under the appropriate buffer conditions) to DCB label the cells.

In certain embodiments, the amount of each of the one or more DCB label(s) in a kit is designed for labeling a specific cell type. As noted above, certain characteristics of the cells may impact the amount and type of DCB label that is required to distinctly DCB mark it (e.g., cells from a particular species, cells of a particular size, whether the cell is fixed and/or permeabilized, etc.). In addition, the kits of the invention may be designed for use with specific flow cytometers (e.g., include DCB labels that can be distinctly detected by a specific configuration of excitation light and/or detection optics).

In certain embodiments, kits of the invention include additional components that find use in performing the DCB methods of the invention. Such additional components include, but are not limited to, buffers for reconstitution and/or dilution of the DCB label, buffers for other steps in the assay (e.g., wash buffers, FACS-compatible buffers, and the like), control cell population(s) (e.g., live cells or fixed and/or permeabilized cells) or beads that can be labeled with the DCB labels and act as DCB labeling controls and/or for calibration of the flow cytometer, fluorescent beads for flow cytometer calibration, binding agents for the detection of a cellular characteristic of interest (e.g., an fluorescent antibody that binds to an antigen of interest), controls for the binding agents (e.g., fluorescent isotype control antibodies), etc.

As with the DCB labels described above, any of the additional components may be provided in any convenient configuration. For example, certain control samples (e.g., cells or beads) may be pre-deposited into a multi-well strip (or plate) at specific locations to ensure that the DCB staining procedure performed as intended and/or that the flow cytometer is performing consistently throughout analysis of the sample.

In certain embodiments, the kits of the invention include instructions for performing the DCB labeling assay for which the kit was designed. Any convenient format for including the instructions may be employed, including providing them written form (e.g., on paper, plastic, or other appropriate substrata), on computer readable media (e.g., CD-ROM, USB memory stick, etc.), or in electronic form (e.g., via email or over the internet).

III. Utility

The methods, systems and kits of the present invention provide significant advantages in analysis of multiple cell samples. These advantages include, but are not limited to, the following.

1) The present invention allows one to combine hundreds, thousands, tens of thousands or more samples into a single analysis tube, thereby increasing the throughput of cell assays that are typically limited because of the number of individual samples that must be analyzed. In other words, the present invention reduces the amount of time needed for data acquisition, saving time and wear on the detector system.

2) The consistency between samples is significantly enhanced. In standard multi-sample cell experiments, variation between samples is high due to slight differences cell handling for each sample. Variation is also caused by fluctuation in the performance of the detection system during the data acquisition process (e.g., hardware such as lasers, detectors, and analog-digital conversion electronics can vary during prolonged use). By combining multiple samples into one sample, these sources of variation are significantly reduced, if not completely eliminated. Cells are stained in the same volume, with the same concentration of reagents, and are measured on the detection system at the same time (thus, the multiplex sample faces the same hardware variations should they occur). This also increases the value of control samples, as it obviates the uncertainty related to potential pipetting/deposition errors (e.g., a negative result being due to the failure to add an antibody to a sample rather than being truly negative for the analyte of interest).

3) The amount of reagents (e.g., antibodies) required to stain combined samples is greatly reduced. For example, standard flow cytometric experiments require collection of 10,000-100,000 events (or cells) per sample. However, for efficient staining and data acquisition (which incurs some sample loss), anywhere from 500,000 to 1,000,000 cells are typically stained. Thus, there is a great excess of cells that are stained and not analyzed for every sample analyzed by flow cytometry. In the present invention, the number of cells that are stained can be kept at 1,000,000, but now 20 samples×50,000 cells each can be stained. This allows for at least 10,000 cells to be analyzed for each sample, but has now allowed the use of 1/20 the amount of antibody, since the total cell number has not changed. This is significant in high-throughput drug screens or large scale experiments, because antibody costs can be very high (e.g., 100 samples stained with 5 different antibodies can easily cost $2,000 or more). As such, cutting these costs by 90-95% makes large scale experiments much more feasible.

Given these significant advantages, the methods and compositions of the present invention find use in numerous cell assay formats, including in basic research applications, clinical diagnostics, drug screens, and any cellular assay in which multiple samples are analyzed.

Examples

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, and pressure is at or near atmospheric.

While the Examples below are described for FCBs, other DCBs may be employed in a similar manner. As noted above, the molecular mass-based DCB markers that are detected using mass spectrometry may also be employed in the multiplex cellular assays of the present invention. Exemplary methods for mass spectrometer analysis of cells can be found in the following: Ornatsky et al. "Multiple cellular antigen detection by ICP-MS" *J Immunol Methods*. (2006) vol. 308 pp. 68-76; Tanner et al. "Multiplex bio-assay with inductively coupled plasma mass spectrometry: Towards a massively multivariate single-cell technology", *Spectrochimica Acta Part B: Atomic Spectroscopy* (2007) vol. 62 pp. 188-195; each of which is incorporated by reference in its entirety for its description of mass spectrometer-based cell analysis.

I. RESULTS

The FCB Technique

The FCB technique is based largely upon standard phospho flow protocols, with slight modification (ref. 4) (FIG. 2*a*). During methanol permeabilization, each sample is treated with a different concentration and/or combination of amine-reactive fluorescent dyes (FCB markers) to label intracellular proteins. After covalent attachment of the FCB markers, the barcoded samples can be combined and differentiated based on their fluorescence signatures, that is, their fluorescence intensity in the channels corresponding to the FCB dyes used.

We tested four small-molecule fluorescent dyes—Pacific Blue, Alexa 488, Alexa 700 and Alexa 750—as potential FCB markers (FIG. 2*b*). After formaldehyde fixation, we permeabilized the cells with methanol containing four different concentrations of each FCB reagent (an unlabeled sample, that is, zero FCB reagent, was used as the 'lowest' FCB level). All four of the chosen dyes could effectively label four different samples with high resolution.

Deconvolution Methods for FCB Mixed Samples

To test the FCB technique we stimulated U937 monocytes with IFN-γ, IL-4 or the combination IFN-γ+IL-4 for 15 min to induce Stat1 and Stat6 phosphorylation selectively, and barcoded the cells with Pacific Blue at three fourfold dilutions (no dye was added to the lowest FCB level sample; FIG. 3). We combined the samples into one tube, and stained them with Alexa 488-labeled antibodies against phosphorylated Stat1 (pStat1 Alexa 488) and Alexa 647-labeled antibodies against phosphorylated Stat6 (pStat6 Alexa 647).

We then determined whether the mixed sample could be deconvoluted, or unmixed, back into the original individual samples, based on their barcoded fluorescent (or FCB) signatures. Different FCB fluorophores (with different emission wavelengths) can be used simultaneously, each at multiple intensities, to generate a complex signature that can trace the history of where a sample originated, that is, its stimulation or treatment conditions.

After gating on scatter properties, we identified and gated four populations with different Pacific Blue fluorescence intensity. We displayed histograms of each of these populations for their pStat1 and pStat6 levels (FIG. 3). The FCB technique clearly allowed separation of the four samples, and we observed the expected results (IFN-γ induced Stat1 phosphorylation, and IL-4 induced Stat6 phosphorylation, whereas stimulation with both induced both proteins). Because the FCB signature is read first in this approach, we termed this method of analyzing the data 'forward deconvolution'. In a second analytical approach, we first analyzed the mixed sample for Stat1 and Stat6 phosphorylation, and then gated cells in each of the four resulting quadrants (FIG. 3). This display approach is particularly well suited to rapid identification of compounds that induce or inhibit one pathway selectively compared to another. For instance, we could rapidly identify that all of the pStat1-positive, pStat6-negative cells came from the IFN-γ-stimulated sample (sample 2). Because in this method samples are selected for a desired phenotypic effect and then deconvoluted based on their FCB signature, we termed this approach 'reverse deconvolution'. The final analytical method is 'simultaneous deconvolution and analysis' of both the FCB channel and a phospho-protein (FIG. 3). For small sample sets, such as the one illustrated here, this method allows for rapid correlation of stimulation or treatment conditions with phenotypic outcome. Such analysis, however, is limited to one FCB channel at a time, and therefore is restricted to smaller experiments.

The potential for 'spill-over' of samples from one barcoded sample to another could potentially lead to inaccurate analysis, but we observed little such 'cross-contamination'. In fact, samples were typically greater than 99.9% pure.

Efficient Barcoding of Six Samples Per FCB Marker

We tested the separation of six populations per FCB marker. Using Pacific Blue and Alexa 488, we barcoded 36 samples simultaneously by labeling six populations per channel (FIG. 4*a*). Forward deconvolution of one column showed the expected alternating stimulated and unstimulated samples (with a purity of >99%). Reverse deconvolution of basal versus stimulated pStat1 levels revealed the expected checkerboard pattern of the 6×6 array. We analyzed the Z' factor for this experiment as a measure of the robustness of the assay, comparing the median fluorescence intensity of the 18 unstimulated versus 18 stimulated samples, and calculated a score of 0.91. Scores between 0.5 and 1.0 are considered excellent for high-throughput screening and indicate a large separation between positive and negative controls with small standard deviations (ref. 23). Thus, FCB showed remarkable robustness in maintaining sample integrity even in a 6×6 matrix.

We typically combined barcoded samples to a total concentration of one million cells, using approximately 100,000 cells per sample. But in 36-96-sample experiments, such as outlined here, more than 1 million cells had to be combined and stained, raising a concern over the effect of increasing the ratio of cells to antibody concentration (see below). Increasing the number of cells to 5 million per stain increased the coefficient of variation (CV) of phospho-antibody staining 3-5%, with CVs typically in the range of 50-70% (FIG. 7). These changes were imperceptible when viewing the data, and did not adversely affect the fold changes measured. Therefore, with most monoclonal phospho antibodies, it is possible to stain at least five times the typical cell number used, and still obtain nearly identical staining characteristics and fold changes.

Miniature Drug Screening with Six Samples

We next applied the FCB platform to a drug screening profile, as a real-world example of how the technique could be used to enhance analysis throughput and reproducibility (FIG. 4*b*). Using Pacific Blue as the FCB reagent, we pretreated U937 cells with four small-molecule inhibitors: wortmannin (a PI-3 kinase inhibitor), Jak inhibitor I (an inhibitor of all Jak kinases), PD98059 (an MEK inhibitor) and WHI-P154 (a Jak3 inhibitor). We then stimulated the cells simultaneously with IFN-γ, IL-6 and granulocyte-monocyte colony-stimulating factor (GM-CSF) to induce pStat1, pStat3 and pStat5, respectively. At a concentration of 5 μM, Jak inhibitor I inhibited all three signaling pathways, completely abrogating Stat1, Stat3 and Stat5 phosphorylation. WHI-P154 had more variable effects, inhibiting Stat3 phosphorylation 100%, Stat1 phosphorylation 80%, and Stat5 phosphorylation 40%. Wortmannin and PD98059 exerted no or minor effects on Stat signaling.

We next performed titration experiments with Jak inhibitor I and WHI-P154 to determine their selectivity for each of the cytokine pathways. Both compounds showed the following order of selectivity: IL-6-Stat3>IFN-γ-Stat1>GM-CSF-Stat5, even though WHI-P154 is a putative Jak3-selective inhibitor, and Jak inhibitor I is a more general inhibitor. Notably, we included both positive and negative controls in each titration, permitting determination of percent inhibition from samples stained by the same antibody cocktail and effectively eliminating pipetting and staining error.

Drug Screening in 96-Well Plates: Multiple Pathway Analysis

Because most cell-based high-throughput screens use 96-well microtiter plates, we next addressed the question whether the technique could be adapted to a 96-well plate. For this purpose, we designed an FCB labeling scheme using three dyes to barcode 96 samples (FIG. 5). With this FCB setup, we screened a small-molecule library of 70 previously characterized kinase and phosphatase inhibitors for their ability to inhibit T-cell receptor-mediated ERK phosphorylation and/or Stat1 phosphorylation induced by IFN-γ (FIG. 5*a*). After addition of inhibitors, stimulation, fixation and barcoding, we combined all 96 samples into one sample and stained it with phycoerythrin-labeled antibodies against phosphorylated ERK (pERK PE) and pStat1 Alexa 647 antibodies (for a total of five fluorophores: three FCB reagents and two antibodies). Using the first and last control columns, the average fold change of phosphorylation upon stimulation was 5.8 for Stat1 and 4.5 for ERK (FIG. 5*c*). We also calculated the Z' factor from these samples, and it was 0.71 for Stat1 and 0.69 for ERK, indicating robust assay performance.

This 'small-scale' screening produced several hits, both expected and unexpected. The major advantage of phospho flow in drug screening lies in the ability to immediately discern compound selectivity for one pathway over another in single cells. Indeed, we were able to identify three classes of drug activity in our assay (FIG. 5*d*). The first class showed selectivity for inhibiting Stat1 phosphorylation and included indirubin-3'-monooxime (well G10; putative CDK inhibitor) (ref. 24) and to a lesser extent SP-600125 (G8; putative Jun N-terminal kinase (JNK) inhibitor). The second class selectively inhibited ERK phosphorylation and included U0126 (B2; MEK inhibitor), sphingosine (D10; a PKC inhibitor) and PP2 (F4; an Src inhibitor). The third class of compounds inhibited both Stat1 and ERK phosphorylation potently, and included staurosporine (B6) and ZM-449829 (G4; a putative Jak3 kinase inhibitor). Bay11-7082 (G5; a putative IB kinase inhibitor) inhibited Stat1 phosphorylation potently, but also inhibited ERK phosphorylation 50%. Owing to the logarithmic scale of flow cytometry data, this 50% inhibition does not appear to be a large shift (in this case downward). It is therefore important to rely on calculations rather than visual observation of flow data when determining selectivity of inhibitors.

Because a few of these hits were unexpected, we performed titration experiments using six-sample FCB on four of the compounds to validate the results (FIG. 8). We found that PP2 and indirubin-3-monooxime were extremely selective for ERK and Stat1, respectively, whereas ZM-449829 and Bay-11-7082 showed little selectivity. These results underscore that the claimed target specificity of kinase inhibitors should be cautiously considered when using these compounds in cell-based assays.

Through this compound screen, we were able to readily identify two compounds that showed selectivity for one signaling pathway over the other and three compounds that blocked both pathways. Notably, the entire experiment took approximately 5 min to run on the flow cytometer, and used only one 'test'-worth of each antibody.

Signaling Profiling in Primary Heterogeneous Cell Populations

Primary cells, and diseased cells from patients, are a limited resource and are not amenable to the majority of high-throughput screening systems. Therefore, we tested whether FCB could be applied to large-scale signaling profiling of heterogeneous populations of normal and/or diseased cells (refs. 13, 14). To this end, we stimulated primary mouse splenocytes with IFN-γ in a 96-well plate format, and asked whether different cell types show different kinetics and thresholds of responsiveness to IFN-γ. We performed a time course of stimulation across 11 different concentrations of the cytokine. Here, to discriminate cell types in addition to measuring phosphorylation levels, we stained the cells with pStat1 Alexa 647 and four surface marker antibodies: B220, TCR, CD4 and CD11b (for a total of eight colors: three FCB markers, four surface antibodies and one phospho antibody). We first gated cell types based on surface marker expression to obtain B cells, CD4+ T cells, CD4− T cells and CD11b-hi cells (neutrophils) 25 (FIG. 6*a*). We then deconvoluted each cell type to obtain the original plate layout.

We obtained several results from this time course and dose titration experiment (FIG. 6*b*). First, B cells and CD4+/CD4− T cells showed a robust, 19-23-fold maximum induction of pStat1 in response to IFN-γ stimulation, whereas neutrophils only showed a maximum 4.5-fold induction of pStat1. Second, after plotting the fold responses against IFN-γ concentration at each time point, we found the four cell types showed different sensitivity to the cytokine. T cells were the most sensitive, with both CD4+ and CD4− T cells displaying a half-maximal response concentration (EC50) of 50 pg/ml. B cells followed with fourfold lower sensitivity (EC50 of 220 pg/ml), and neutrophils were least sensitive (EC50 of 400 pg/ml). The Hill coefficient of the titration curves correlated inversely with the EC50 values, such that T cells had the lowest Hill coefficient (1.3), B cells were intermediate (1.65) and neutrophils had the highest (2.0). This indicates that T cells can sense a broader range of IFN-γ from the unstimulated to fully stimulated state than B cells and neutrophils. Finally, the time of maximal pStat1 induction differed among the cell types. B cells showed maximal response from 8-30 min, whereas T cells peaked at 30 min. Neutrophils responded most slowly, reaching maximum induction at 30-60 min. These results clearly demonstrate the power of phospho flow in discerning cell type-specific effects of stimulation and the utility of FCB in allowing rapid, cost-effective large-scale profiling.

II. DISCUSSION

We demonstrate application of the technique to barcoding of 96 samples simultaneously with excellent resolution, both in cell lines and in primary mouse splenocytes. Antibody consumption was reduced 100-fold and acquisition time was reduced to 5-15 min per 96-well plate. These advances make large-scale drug screening and disease signaling profiling more feasible on the flow cytometry platform in standard laboratory settings, and will permit experiments that were previously deemed unfeasible owing to cost or acquisition time. The present invention provides methods for this approach.

Using FCB and phospho-specific flow cytometry, we screened a small-molecule library for inhibitors of T cell-receptor and cytokine signaling, simultaneously determining compound efficacy and selectivity. We also analyzed IFN-γ signaling in multiple cell types from primary mouse splenocytes, revealing differences in sensitivity and kinetics between B cells, CD4+ and CD4− T cells and CD11b-hi cells.

Although the FCB method is robust, several important technical considerations should be kept in mind when first applying the technique.

First are cell type differences. The amount of dye that optimally labels cells will differ with the cell line or primary cell population of interest, and therefore titration of the FCB reagent is required. It is also important to gate heterogeneous primary cell populations into individual cell types before analysis of the FCB channel, as T cells and B cells differ substantially in size compared to macrophages or dendritic cells. This size difference can lead to errors in FCB deconvolution.

Second is the concentration of FCB markers. Use of higher concentrations of dyes labeled samples with more fluorescence, but also caused unstained populations to show substantial fluorescence upon mixing of all the samples. This was likely due to residual (<0.1%) amounts of reactive dyes left after washing or transfer of small amounts of proteins between cells. We found two solutions for this problem: washing samples thoroughly and using a smaller quantity of reactive dye (3 μg/ml or less for the brightest population) to maintain unstained samples as close to autofluorescence levels as possible (see Supplementary Methods online).

Third is the resolution and purity of deconvoluted samples. We observed that samples can be analyzed at greater than 99.9% purity once optimal labeling levels have been determined with four to six levels of FCB markers. For cell lines, we typically observed CVs of 20-30% for the individual levels of the FCB marker (with Pacific Blue and Alexa 488 showing lower CV values than Alexa 700). Because approximately 70% of a population falls within 1 s.d. (CV=s.d./mean of population), one can gate extremely tightly on the FCB channel, and still obtain 70% of each of the respective samples. Purity of the samples is determined by the lack of contamination from neighboring samples, which is based on the distance between the medians and the CV. If medians are separated by threefold increases, the central 70% of each population will contain less than 5% contamination from any neighboring populations. Therefore, since flow cytometers are sensitive over a 4-log range (of which about 3.5 logs are usable to keep populations from spilling above or below scale), seven populations could theoretically be discerned with >95% purity on each FCB. In actual practice, we have shown that six FCB levels can be distinguished with >99% purity. We have also labeled seven populations with one FCB marker (data not shown). The enhanced purity relative to theoretical prediction lies in the fact that one can gate the FCB channel in relation to forward or side scatter, both of which correlate closely to FCB level. That is, as cell size increases, FCB staining increases. In fact, the correlation appears to be nearly 1:1 for U937 cells and Pacific Blue as the FCB marker. In our primary mouse splenocyte experiment, CVs of T cells and B cells for Alexa 488 and Pacific Blue were typically 15-20%, likely as a result of the narrower size distribution and uniformity of the cells.

Fourth is the number of cells required for combined samples. An inherent advantage of the FCB technique is that most of the cells that are stained are actually collected and analyzed on the flow cytometer. In standard methods, over 95% of the stained sample is usually not analyzed. In the FCB method, we typically combined five times more cells than were required for analysis and stained only those. For instance, if ten samples were barcoded, and we required 10,000 cells per sample, we combined approximately 50,000 cells from each sample to obtain 500,000 total cells. For 96-well plate experiments in Jurkat cells, 1 million cells were required (96×10,000); therefore we stained 5 million cells. For primary cells, we stained 20 million cells. This is important to note because cell number can affect staining robustness. We found, however, that even if we combine six samples in their entirety (approximately 5 million total cells) versus staining those samples separately (approximately 1 million cells each), the CV and median of each sample did not change appreciably (FIG. 7).

Finally are the analytical methods available to analyze complex flow cytometric data. Standard flow cytometry analysis software (such as FlowJo; Tree star Inc.) is designed to efficiently compare parameters, such as phospho-protein staining levels, between different samples but not dozens of subpopulations within one sample (as is done in the FCB multiplex analysis described herein). As such, new software tools specifically designed to rapidly deconvolute and analyze all of the sample populations within the combined samples used by FCB are of interest. We are currently developing and implementing such tools in our laboratory.

Here we applied the FCB platform to phospho flow, which has a critical advantage for drug screening in its ability to immediately analyze drug selectivity for a particular pathway among other pathways, eliminating follow-up on nonspecific drugs that inhibit multiple pathways simultaneously. In areas of interest to those researchers monitoring signaling events in complex populations of cells, the FCB technique can be used during late-stage clinical monitoring of drug efficacy directly from patient blood samples. We believe that FCB will allow flow-cytometric analysis, and its wide range of single cell-based assays, to be applied to large-scale disease profiling efforts as well as high-throughput drug screening.

III. MATERIALS AND METHODS

Reagents.

FCB reagents included amine-reactive Alexa Fluor succinimidyl esters (NHS) (Alexa 488-NHS, Alexa 700-NHS and Alexa 750-NHS) and Pacific Blue succinimidyl ester (Pacific Blue-NHS) from Molecular Probes. Phospho-specific antibodies to Stat1 (pY701), Stat3 (pY705), Stat5 (pY694), Stat6 (pY641), and ERK1/2 (pT202/pY204) conjugated to Alexa 488, PE or Alexa 647 and surface marker antibodies to mouse TCR(H57-597), CD11b (M1/70), B220 (RA3-6B2), CD4 (RM4-5) and human CD3 (UCHT1) and CD28 (CD28.2) were kindly provided by BD Pharmingen. We conjugated B220 to Quantum Dot 605 using the manufacturer's protocol (Quantum Dot Corporation).

BSA and ethanolamine were from Sigma. Sealed ampules of 16% paraformaldehyde in water were from Electron Microscopy Sciences. Human IFN-γ, GM-CSF, IL-6, and mouse IFN-γ were from BD Pharmingen. The 70-compound kinase-phosphatase inhibitor library was from Biomol. Wortmannin, PD98059, U0126, Jak inhibitor I and WHI-P154 were from Calbiochem.

Cells and Stimulation.

We cultured U937 cells, a monocytic lymphoma cell line, and Jurkat T cells in RPMI-1640 containing 10% fetal bovine serum, 100 U/ml penicillin, 100 μg/ml streptomycin, 1 mM L-glutamine (RPMI-10), and stimulated cells at a density of 106 cells/ml. We obtained splenocytes from BALB/c mice by homogenization and resuspended them in RPMI-10 at 5 106 cells/ml. Splenocytes were rested for 2-3 h at 37° C. before stimulation13. We stimulated cells in 96-well deep block plates (2-ml capacity) by adding the appropriate cytokine or stimulus directly to the culture medium without prior starvation. After a 10-15-min incubation, we fixed cells with 1.6% formaldehyde for 10 min and then proceeded with the FCB phospho flow protocol below. Where inhibitors were used, we added these compounds 30 min before stimulation.

Fluorescent Cell Barcoding Phospho Flow.

We performed phospho flow as previously described (ref. 4) with slight modifications to include FCB labeling. After formaldehyde fixation, we resuspended samples in 100% 20-25° C. methanol (typically 500 μl per $10^6$ cells) containing the indicated concentration of Alexa Fluor or Pacific Blue succinimidyl esters, with each sample receiving a different concentration of fluorescent dye. In some cases, we resuspended samples in methanol and then added FCB fluorophores dissolved in DMSO (typically at 1:50 dilution). This was done to allow prior preparation and storage of FCB staining matrices in DMSO, necessary for 96-well plate experiments. After labeling for 15 min at 20-25° C., we washed cells twice with staining medium (phosphate-buffered saline (pH 7.0) containing 0.5% BSA and 0.02% sodium azide). We observed that labeling at 4° C. or colder produced very low labeling intensities, allowing storage of samples at −80° C. in the methanol staining solution without increasing FCB staining levels4.

We then combined the differentially labeled samples into one FACS tube or well, and pelleted them again if the resulting volume was greater than 100 μl. We stained the combined, barcoded sample (typically 100 μl) with phospho-specific and/or surface marker antibodies, washed and analyzed them by flow cytometry. Flow cytometry was performed on a BD LSR2 flow cytometer, equipped with 405 nm, 488 nm and 633 nm lasers, and manufacturer's stock filters, with replacement of the 405 nm octagon bandpass filter for Cascade Yellow with a 610/20 bandpass filter for detection of Quantum Dot 605.

FCB Dye Concentration

Note that in the 6×6 matrix experiment and 6 level miniature drug screen, we used high concentrations of FCB reagents (up 40 μg/ml). We have found that although this method worked well, unstained samples showed increased fluorescence after combination with highly labeled samples (even after washing and quenching) and overall fluorescence intensities were high, requiring reduction in typical PMT settings on the flow cytometer. Labeling with lower concentrations of FCB reagents (3 μg/ml and below) eliminated this increase in background staining of unstained samples, and therefore maintained excellent separation between samples without requiring adjustment of typical PMT settings. This also reduced fluorophore consumption 10-fold and reduced cost dramatically. We therefore used 3 μg/ml or less of the FCB reagents (except for Ax750 which is dimmer, and requires 10 μg/ml) for subsequent 96-well plate experiments.

Calculations

We calculated fold change of phosphorylation upon stimulation by dividing median fluorescence intensity (MFI) of stimulated samples by the MFI of unstimulated samples: $FC=MFI_{stim}/MFI_{unstim}$. For heat map analysis, FC was converted to $\log_2$ values to enhance visualization and so that samples showing no change have a value of zero. To measure drug activity, we calculated percent inhibition as follows: Percent Inhibition$=1-((MFI_{treated}-MFI_{unstim})/(MFI_{stim}-MFI_{unstim}))$, where "treated" denotes drug treated (and stimulated) samples, "stim" denotes control stimulated (non drug treated) samples, and "unstim" denotes control unstimulated (non drug treated) samples. We calculated Z'-factor from control stimulated and unstimulated samples by the following: Z'-factor$=1-((3\square SD_{stim}\ 3\square SD_{unstim})/(mean_{stim}-mean_{unstim}))$, where "SD" denotes standard deviation of the mean, and "mean" denotes the mean of either stimulated or unstimulated MFI values. Z'-factor is an indication of the robustness and suitability of an assay for high throughput screening, with values from 0.5 to 1 indicating an excellent assay, 0 to 0.5 indicating a usable assay, and less than 0 indicating the assay has too much noise or inadequate dynamic range.

IV. REFERENCES

1. Tung, J. W., Parks, D. R., Moore, W. A., Herzenberg, L. A. & Herzenberg, L. A. Identification of B-cell subsets: an exposition of 11-color (Hi-D) FACS methods. Methods Mol. Biol. 271, 37-58 (2004).
2. De Rosa, S. C., Herzenberg, L. A., Herzenberg, L. A. & Roederer, M. 11-color, 13-parameter flow cytometry: identification of human naive T cells by phenotype, function, and T-cell receptor diversity. Nat. Med. 7, 245-248 (2001).
3. Krutzik, P. O., Irish, J. M., Nolan, G. P. & Perez, O. D. Analysis of protein phosphorylation and cellular signaling events by flow cytometry: techniques and clinical applications. Clin. Immunol. 110, 206-221 (2004).
4. Krutzik, P. O. & Nolan, G. P. Intracellular phospho-protein staining techniques for flow cytometry: monitoring single cell signaling events. Cytometry A 55, 61-70 (2003).
5. Fleisher, T. A. et al. Detection of intracellular phosphorylated STAT-1 by flow cytometry. Clin. Immunol. 90, 425-430 (1999).
6. Sachs, K., Perez, O., Pe'er, D., Lauffenburger, D. A. & Nolan, G. P. Causal protein-signaling networks derived from multiparameter single-cell data. Science 308, 523-529 (2005).
7. Ilangumaran, S., Ramanathan, S., La Rose, J., Poussier, P. & Rottapel, R. Suppressor of cytokine signaling 1 regulates IL-15 receptor signaling in CD8+CD44 high memory T lymphocytes. J. Immunol. 171, 2435-2445 (2003).
8. Krutzik, P. O., Clutter, M. R. & Nolan, G. P. Coordinate analysis of murine immune cell surface markers and intracellular phosphoproteins by flow cytometry. J. Immunol. 175, 2357-2365 (2005).
9. Ilangumaran, S., Finan, D. & Rottapel, R. Flow cytometric analysis of cytokine receptor signal transduction. J. Immunol. Methods 278, 221-234 (2003).
10. Kersh, E. N. et al. TCR signal transduction in antigen-specific memory CD8 T cells. J. Immunol. 170, 5455-5463 (2003).
11. Chow, S., Patel, H. & Hedley, D. W. Measurement of MAP kinase activation by flow cytometry using phospho-specific antibodies to MEK and ERK: potential for pharmacodynamic monitoring of signal transduction inhibitors. Cytometry 46, 72-78 (2001).
12. Zell, T. et al. Single-cell analysis of signal transduction in CD4 T cells stimulated by antigen in vivo. Proc. Natl. Acad. Sci. USA 98, 10805-10810 (2001).
13. Krutzik, P. O., Hale, M. B. & Nolan, G. P. Characterization of the murine immunological signaling network with phosphospecific flow cytometry. J. Immunol. 175, 2366-2373 (2005).
14. Irish, J. M. et al. Single cell profiling of potentiated phospho-protein networks in cancer cells. Cell 118, 217-228 (2004).
15. Clutter, M. R., Krutzik, P. O. & Nolan, G. P. Phospho-specific flow cytometry in drug discovery. Drug Discov. Today Technol. 2, 295-302 (2005).
16. Jacobberger, J. W. et al. Immunoreactivity of Stat5 phosphorylated on tyrosine as a cell-based measure of Bcr/Abl kinase activity. Cytometry A 54, 75-88 (2003).
17. Kuckuck, F. W., Edwards, B. S. & Sklar, L. A. High throughput flow cytometry. Cytometry 44, 83-90 (2001).
18. Edwards, B. S., Oprea, T., Prossnitz, E. R. & Sklar, L. A. Flow cytometry for high-throughput, high-content screening. Curr. Opin. Chem. Biol. 8, 392-398 (2004).
19. Nam, J. M., Thaxton, C. S. & Mirkin, C. A. Nanoparticle-based bio-bar codes for the ultrasensitive detection of proteins. Science 301, 1884-1886 (2003).
20. Fulton, R. J., McDade, R. L., Smith, P. L., Kienker, L. J. & Kettman, J. R., Jr. Advanced multiplexed analysis with the FlowMetrix system. Clin. Chem. 43, 1749-1756 (1997).
21. Vignali, D. A. Multiplexed particle-based flow cytometric assays. J. Immunol. Methods 243, 243-255 (2000).
22. Bradford, J. A., Buller, G., Suter, M., Ignatius, M. & Beechem, J. M. Fluorescence-intensity multiplexing: simultaneous seven-marker, two-color immunophenotyping using flow cytometry. Cytometry A 61, 142-152 (2004).
23. Zhang, J. H., Chung, T. D. & Oldenburg, K. R. A simple statistical parameter for use in evaluation and validation of high throughput screening assays. J. Biomol. Screen. 4, 67-73 (1999).
24. Nam, S. et al. Indirubin derivatives inhibit Stat3 signaling and induce apoptosis in human cancer cells. Proc. Natl. Acad. Sci. USA 102, 5998-6003 (2005).
25. Lagasse, E. & Weissman, I. L. Flow cytometric identification of murine neutrophils and monocytes. J. Immunol. Methods 197, 139-150 (1996).

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

The scope of the present invention, therefore, is not intended to be limited to the exemplary embodiments shown and described herein. Rather, the scope and spirit of the present invention is embodied by the appended claims.

What is claimed is:

1. A method of detecting a characteristic of cells in multiple cell samples, said method comprising:

a) contacting multiple cell samples with a different amount of a first detectable cell barcode (DCB) label having a first detectable characteristic thereby generating multiple differentially labeled cell samples, wherein said first DCB label binds to the cells in said multiple cell samples;

b) combining said multiple differentially-labeled cell samples to produce a combined cell sample;

c) analyzing the cells in said combined cell sample to detect:

i) the amount of said first detectable characteristic on said cells in said combined cell sample; and ii) at least one second detectable characteristic of said cells in said combined cell sample;

to obtain a result, wherein detection of said first detectable characteristic does not interfere with detection of said at least one second detectable characteristic of said cells in said combined cell sample, and d) deconvoluting said result based on said detected amount of said first detectable characteristic on said cells to detect said at least one second detectable characteristic of said cells in each of said multiple cell samples.

2. The method of claim 1, wherein said analyzing step is carried out by flow cytometry.

3. The method of claim 1, wherein said analyzing step is carried out by mass spectrometry.

4. The method of claim 1, wherein said first DCB label is functionalized to bind covalently to said cells.

5. The method of claim 1, wherein said first DCB label is functionalized to bind non-covalently to said cells.

6. The method of claim 4, wherein said first DCB label is functionalized with a covalent cell binding moiety selected from one or more of: amine-reactive groups, thiol-reactive groups, hydroxyl reactive groups, aldehyde-reactive groups, isothiocyanate groups, amino groups, haloacetyl groups, maleimides, succinimidyl esters, thiols, aldehydes, hydrazides, and sulfonyl halides.

7. The method of claim 5, wherein said first DCB label is functionalized with a non-covalent cell binding moiety that binds to said cells via an interaction selected from: hydrophobic, hydrogen-bonding, Van der Waals, ionic interactions, and combinations thereof.

8. The method of claim 1, wherein said first detectable characteristic is selected from: fluorescence emission wavelength, fluorescence polarization, fluorescence lifetime, light scatter, molecular mass, and combinations thereof.

9. The method of claim 1, wherein multiple DCB labels each having a distinct detectable characteristic are employed in said differential labeling step, wherein the amount of each of said distinct detectable characteristic on said cells is detected in said analyzing step, and wherein said deconvoluting is based on the amount of each of said distinct detectable characteristic on said cells.

10. The method of claim 1, wherein said second detectable characteristic includes one or more of: fluorescence emission, fluorescence polarization, fluorescence lifetime, physical property, number, frequency, intensity, molecular mass and combinations thereof.

11. The method of claim 10, wherein said second detectable characteristic is a physical property, wherein said physical property is selected from one or more of: cell size, cell shape, and cell granularity.

12. The method of claim 1, wherein said at least one second detectable characteristic is the presence of one or more analyte in or on said cells.

13. The method of claim 12, wherein said combined cell sample is contacted to one or more detectable binding agent specific for said one or more analyte prior to said analyzing step.

14. The method of claim 13, wherein said one or more analyte is selected from one or more of: protein, carbohydrate, organelle, nucleic acid, infectious particle, metabolite, ion, and combination thereof.

15. The method of claim 14, wherein said infectious particle is selected from one or more of: virus, bacteria, parasite and combinations thereof.

16. The method of claim 12, wherein said one or more analyte is an isoform of a protein.

17. The method of claim 16, wherein said isoform is a phospho-isoform of said protein.

18. The method of claim 13, wherein said detectable binding agent is a detectable antibody.

19. The method of claim 1, wherein said method is performed on live cells.

20. The method of claim 1, wherein said method further comprises one or both of: fixing said cells and permeabilizing said cells.

21. The method of claim 1, wherein said first DCB label is indirectly detected.

22. The method of claim 16, wherein said protein is a signaling protein and wherein said isoform is an activated isoform of said signaling protein.

23. The method of claim 1, further comprising stimulating one or more of said multiple cell samples with an agonist prior to said combining step.

24. The method of claim 23, wherein a plurality of said multiple cell samples are each stimulated with a different agonist.

25. The method of claim 1, further comprising treating one or more of said multiple cell samples with a candidate agent prior to said combining step.

26. The method of claim 25, wherein a plurality of said multiple cell samples are each treated with a different candidate agent.

27. The method of claim 25, further comprising stimulating said treated cell samples with an agonist prior to said combining step.

28. The method of claim 25, wherein said candidate agent is selected from one or more of: a protein, a small molecule, an organic molecule, a carbohydrate, a polysaccharide, a polynucleotide, a polypeptide, and a lipid.

* * * * *